(12) United States Patent
Daghighian et al.

(10) Patent No.: US 8,068,896 B2
(45) Date of Patent: Nov. 29, 2011

(54) DETECTION OF RADIATION LABELED SITES USING A RADIATION DETECTION PROBE OR CAMERA INCORPORATING A SOLID STATE PHOTO-MULTIPLIER

(75) Inventors: Farhad Daghighian, Santa Monica, CA (US); Henry Daghighian, Mountain View, CA (US)

(73) Assignee: Intramedical Imaging, LLC, Los Angeles, CA (US)

( * ) Notice: Subject to any disclaimer, the term of this patent is extended or adjusted under 35 U.S.C. 154(b) by 936 days.

(21) Appl. No.: 11/784,854

(22) Filed: Apr. 9, 2007

(65) Prior Publication Data

US 2010/0198061 A9    Aug. 5, 2010

Related U.S. Application Data

(63) Continuation-in-part of application No. 11/270,906, filed on Nov. 10, 2005, now Pat. No. 7,653,427.

(60) Provisional application No. 60/855,829, filed on Oct. 31, 2006, provisional application No. 60/809,639, filed on May 30, 2006, provisional application No. 60/656,565, filed on Feb. 25, 2005.

(51) Int. Cl.
*A61B 6/00* (2006.01)
(52) U.S. Cl. .......... 600/436; 250/252; 250/363
(58) Field of Classification Search .......... 600/407; 128/653–654
See application file for complete search history.

(56) References Cited

U.S. PATENT DOCUMENTS

| | | | | |
|---|---|---|---|---|
| 4,005,292 A * | 1/1977 | Oesterlin et al. | ............... | 250/364 |
| 5,008,546 A * | 4/1991 | Mazziotta et al. | ............ | 250/366 |
| 5,325,855 A * | 7/1994 | Daghighian et al. | .......... | 600/407 |
| 5,744,805 A * | 4/1998 | Raylman et al. | ......... | 250/370.01 |
| 5,952,664 A * | 9/1999 | Wake et al. | ................. | 250/459.1 |
| 6,671,541 B2 * | 12/2003 | Bishop et al. | ................. | 600/436 |
| 6,973,163 B2 * | 12/2005 | Arakawa | ......................... | 378/63 |
| 2001/0056234 A1 * | 12/2001 | Weinberg | ...................... | 600/436 |
| 2005/0236553 A1 * | 10/2005 | Noto et al. | .................. | 250/208.1 |
| 2006/0192128 A1 * | 8/2006 | Benlloch Bavciera et al. | ............................ | 250/369 |

* cited by examiner

*Primary Examiner* — Tse Chen
*Assistant Examiner* — Joel F Brutus
(74) *Attorney, Agent, or Firm* — Koppel, Patrick, Heybl & Philpott; Michael J. Ram

(57) ABSTRACT

Intraoperative radiation detection probes and cameras for use in surgical or transcutaneous procedures or procedures incorporating probes inserted through body orifices to aid in the location, detection and removal of radiation labeled cells, abnormal tissue or deposits thereon incorporate solid state or silicon photomultiplier (SSPM, or SiPM) devices to provide safe, highly sensitive and compact beta and gamma probes or cameras for use in locating the radiation labeled sites within the human body or abnormal labeled sites within the body. The probes may include both gamma and beta detecting components as well as means for enhancing the accuracy and sensitivity of the beta detectors.

12 Claims, 12 Drawing Sheets

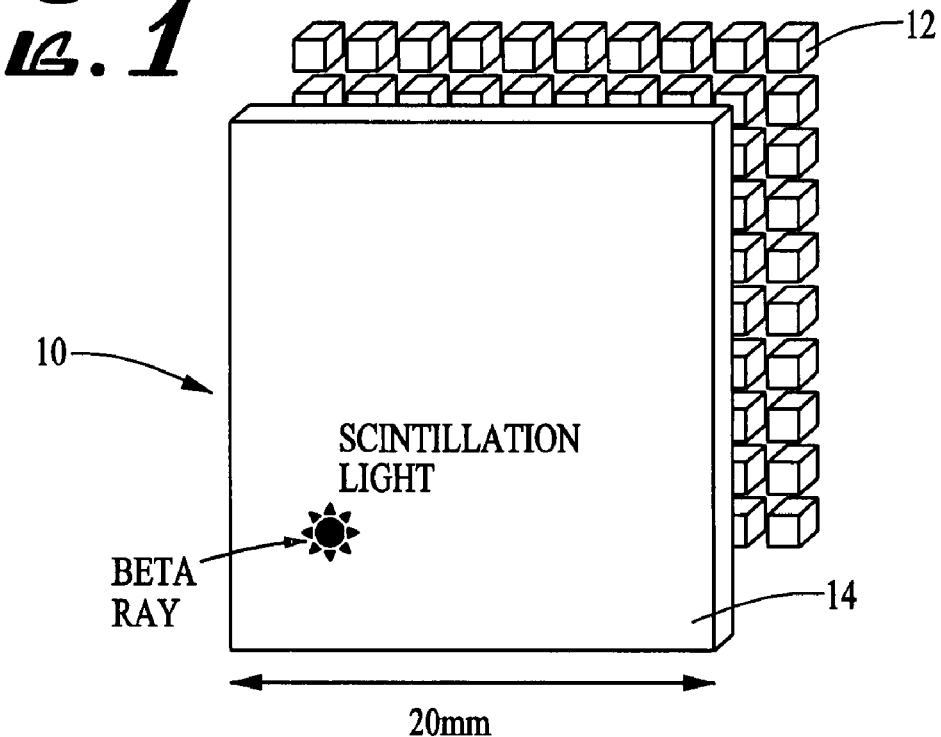
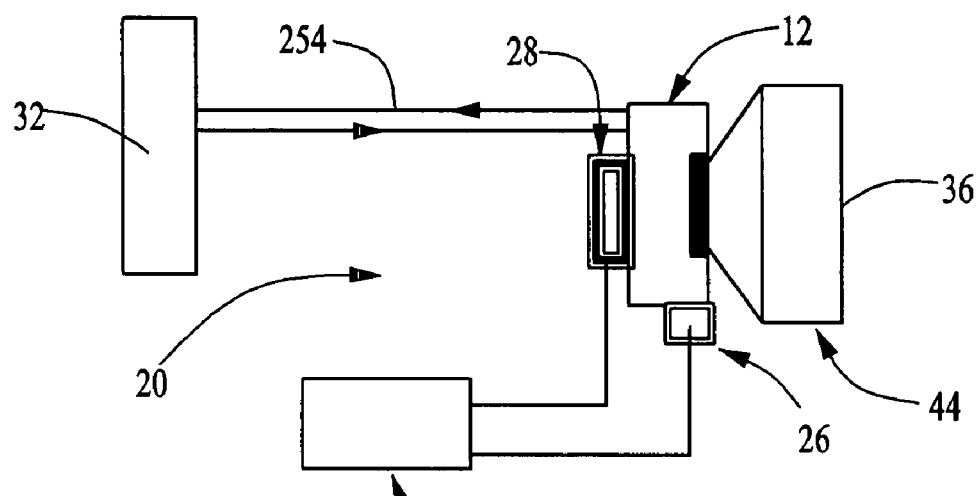

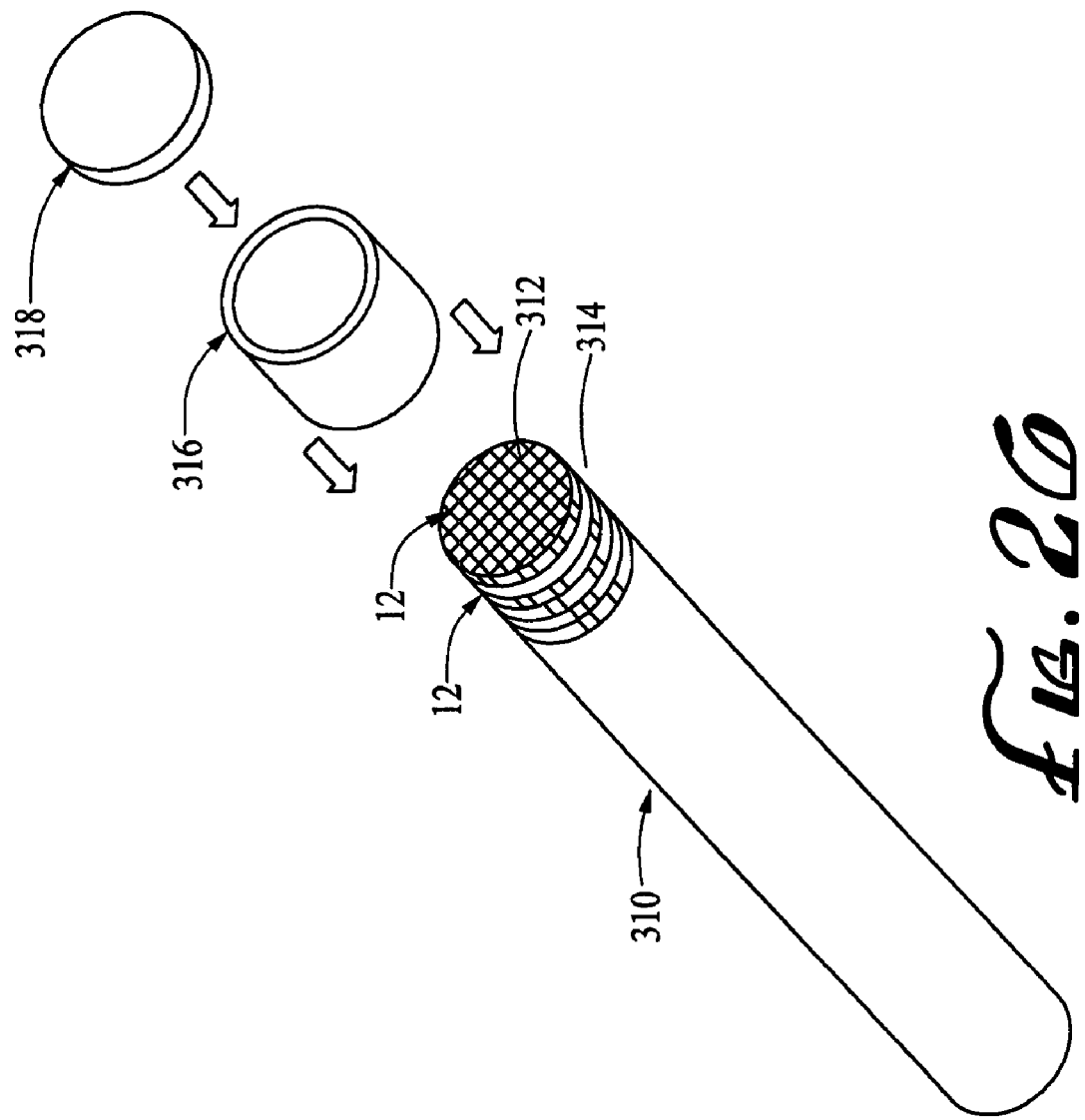

DETECTION OF RADIATION LABELED SITES USING A RADIATION DETECTION PROBE OR CAMERA INCORPORATING A SOLID STATE PHOTO-MULTIPLIER

This application claims benefit of Provisional Application 60/855,829, filed Oct. 31, 2006 and Provisional Application 60/809,639 filed May 30, 2006 and is a Continuation-In-Part of U.S. application Ser. No. 11/270,906 filed Nov. 10, 2005, now U.S. Pat. No. 7,653,427 which claims benefit of U.S. Provisional Application Ser. No. 60/656,565 filed Feb. 25, 2005.

The present invention is directed to the uses of solid state or silicon photomultiplier (SSPM, or SiPM) devices to provide safe, highly sensitive and compact beta and gamma probes or cameras for use for locating radiation labeled sites within the human body. These instruments are intraoperative radiation detection probes for use in surgical procedures to aid in the location, detection and removal of detected cancer cells, as a part of biopsy devices or catheters, configured for delivery through or with a laparoscope for locating and treating abnormal labeled sites within the body, or for examining excised tissue.

BACKGROUND

Surgery is the only certain cure for cancer; however, its curative ability is compromised by the potential of leaving behind microscopic traces of the tumor, known as margins. In breast cancer, for example, there is a 20% recurrence rate after breast-conserving surgery (lumpectomy) due to missed margins. A beta camera capable of surveying the tumor bed, intraoperatively, and imaging visually undetectable, minute amounts of cancer cells, could significantly reduce recurrence rate of many cancers and increase survival. In addition, this beta camera may enable more breast cancer patients to become candidates for breast saving lumpectomies and improve the psychological recovery from breast cancer.

Surgery is an important mode of treatment of prostate cancer. However, several problems remain. Complete local resection of cancerous tissue is not possible in some cases since normal and prostate cancer tissues are not visually distinguishable. In approximately 30% of cases the margins of resection are involved (or positive). Unfortunately, this finding is currently made by the pathologist from the resected prostate, well after the surgery, when there is little that can be done to rectify the situation. Further, assessment of lymph nodes is important in staging the cancer. This is done by multiple node dissections and pathological evaluations in the vast majority of patients, which results in increased morbidity, operative time, and cost. Currently, trans-rectal biopsies, in post-prostatectomy patients with elevated PSA, are done with ultrasound guidance. However, often no suspicious lesion is seen and biopsies are little more than random samples. As a result, there is a low sensitivity rate.

Vulnerable atherosclerotic plaques are the major cause of sudden cardiac death. Detection of this type of plaques is a major challenge in cardiology. Various radiopharmaceuticals have been developed to this date with preferential uptake in vulnerable plaques. Vulnerable plaque (VP) is atherosclerotic plaque that is prone to disruption, causing thrombosis, which often leads to a clinical event. Autopsy studies have demonstrated that the majority of cases of sudden death are caused by occlusive coronary thromboses that are associated with an underlying ruptured plaque. From such autopsy studies, much has been learned about the morphological features that are common to VP. Those histologic characteristics include a thin fibrous cap, an underlying lipid pool, and an abundance of inflammatory cells.

Even with today's best available technology an unacceptably high incidence of cardiovascular events remains even after aggressive therapy. Novel approaches to prevent myocardial infarctions are therefore needed. It is proposed that one of the most effective methods to prevent MI would be to stabilize vulnerable plaque before they rupture. However, currently available systemic therapies are able to lower the risk of plaque rupture by only 20-40%, leaving the vast majority of vulnerable plaques ripe for rupture. As such, it is crucial that vulnerable plaques are localized such that local plaque-stabilizing therapies can be delivered. However, currently available technologies are not able to detect vulnerable plaques. This may be due to the fact that available technologies rely on identifying structural criteria to differentiate the common stable plaque from the rupture-prone vulnerable plaque. Indeed, the most commonly employed method for plaque characterization is coronary arteriography, a method which qualifies plaques based on the degree to which they impinge on and thus narrow the vessel lumen. Multiple angiographic studies that have examined ruptured plaques have found that they are most often associated with insignificant luminal narrowing prior to their rupture. Therefore, technologies that rely on identifying luminal narrowing are not able to identify vulnerable plaques with acceptable sensitivity.

Further, inflammation is particularly important in the development and progression of atherothrombosis. It is now well-established that atherosclerosis is an inflammatory disease. Histopathological data has confirmed the critical association of plaque inflammation and rupture. Numerous studies demonstrate an abundance of inflammatory cells (T cells and macrophages) within ruptured plaques. Moreover, several large studies have shown a strong association between inflammatory biomarkers and subsequent events. Positron emission tomography (PET) may represent the most promising non-invasive imaging technology for the detection of inflammation in humans. PET imaging with $^{18}$F-Flurodeoxyglucose (FDG) has been used extensively in humans to detect metabolically active tissues such as neoplasms, autoimmune disease, and infection. Numerous studies demonstrate that FDG uptake is increased in inflamed tissues such as tumors and infectious foci. Autoradiographic studies show that FDG localizes to macrophage-dense regions within chronic inflammatory lesions and within macrophages surrounding malignant foci.

F-18 atoms emit positrons (beta rays) that in turn generate gamma rays. Gamma rays travel tens of cm in tissue, while beta rays have a range of ~2 mm. Beta emitting isotopes are ideal for intraoperative imaging since background radiation will not interfere with the identification of margins. Until now, beta cameras have suffered from serious flaws that prevent their general use in cancer surgery or in vivo diagnostic procedures. The thin shielding required for positron detection provides insufficient insulation from the high voltage photomultiplier tubes (PMTs) and the long fiber-optic coupling used to separate the high voltage from the patient can greatly reduces sensitivity.

Numerous studies have demonstrated PET's enhanced sensitivity and specificity for identifying tumors as compared to more conventional techniques (Finkelstein S E, Carrasquillo J A, Hoffman J M, Galen B, Choyke P, White D E, Rosenberg S A, Sherry R M. "A Prospective Analysis Of Positron Emission Tomography And Conventional Imaging For Detection Of Stage IV Metastatic Melanoma In Patients Undergoing Metastasectomy", *Ann Surg Oncol,* 11, p 731-

738 (2004); Gulec S A, Faries M B, Lee C C, Kirgan D, Glass C, Morton D L, Essner R. "The Role Of Fluorine-18 Deoxyglucose Positron Emission Tomography In The Management Of Patients With Metastatic Melanoma: Impact On Surgical Decision Making", *Clin Nucl Med,* 28 p 961-965 (2003); Benard F, Turcotte E. "Imaging In Breast Cancer: Single-Photon Computed Tomography And Positron-Emission Tomography", *Breast Cancer Res,* 7, p 153-162, (2005)). Usually, PET is performed after IV injection of F-18 labeled fluorodeoxy-glucose (FDG), a glucose analog that is transported into cells but can't complete its metabolism like glucose, and hence accumulates in the cells. Cancer cells accumulate more FDG than normal cells; therefore they become more radioactive than the surrounding normal tissue. The positrons that are emitted by F-18 travel a short distance in tissue (~1 mm) and then pair up with an electron and annihilate to two high-energy gamma rays. These high-energy gamma rays each have 511 keV energy, and are emitted simultaneously and back-to-back (at a 180 degree angle to each other). The coincidence detection of these emissions by detectors of a PET scanner determines a line along which the F-18 decay occurred (called the line of response). During the PET scan, a collection of these lines will accumulate in the computer of the PET scanner. Using a tomographic algorithm, a distribution map of FDG accumulation is generated by the collection of lines of responses.

A prerequisite for the accurate identification of cancer with PET is the ability of the radiation source to localize within the tumor, with only minimal or no uptake in adjacent normal tissue, necrotic tissue, or healing tissue. A large number of radioisotopes emit positrons. Notable among them are radioisotopes of carbon, nitrogen, oxygen and fluorine (substituted for hydrogen in many compounds). These are the building blocks of biologic matter. Therefore, the choice for making positron emitting radioisotopes is large. To date, more than 500 radiochemicals have been developed with positron emitting radioisotopes (Quon A, Gambhir S S. "FDG-PET And Beyond: Molecular Breast Cancer Imaging", *J Clin Oncol,* 23, p 1664-1673 (2005)). Although there are a variety of radioisotopes that would be useful for PET imaging based on metabolic properties of malignancy, so far only FDG has gained universal acceptance as a cancer-seeking agent. The use of FDG is based on the concept that tumor tissues grow generally faster than normal tissues, and thus have an increased rate of glucose metabolism. The FDG molecule is transported into cells by facilitative glucose transporters, such as GLUT-1, and is phosphorylated to PDG-6 phosphate by hexokinase (Luigi A, Caraco C, Jagoda E, Eckelman W, Neumann, Ronald. Glut-1 And Hexokinase Expression: Relationship With 2-Fluoro-2-Deoxy-D-Glucose Uptake In A431 And T47d Cells In Culture", *Cancer Res,* 59, p 4709-4714 (1999)). Some cancers also have reduced rates of glucose-6-phosphate metabolism accentuating the phosphorylated deoxyglucose into tumor tissue (Chung J K, Lee Y J, Kim S K, Jeong J M, Lee D S, Lee M S. "Comparison Of [18F]Fluorodeoxyglucose Uptake With Glucose Transporter-1 Expression And Proliferation Rate In Human Glioma And Non-Small-Cell Lung Cancer", *Nucl Med Commun,* 25, p 11-17 (2004); Pugachev A, Ruan S, Carlin S, Larson S, Campa J, Ling C, Humm J. "Dependence Of FDG Uptake On Tumor Microenvironment", *Int J Rad Oncol Biol Phys,* 62, p 545-553 (2005)). This intermediary is trapped in cancer cells because the dephosphorylation reaction is either slow or absent.

The greater uptake of FDG and lower levels of metabolism in more aggressive tumors lead to improved imaging of particular cancers; i.e., more accurate staging. FDG avidity is determined by glycolytic activity of the tumor and the viable tumor volume. Individual cancer types may show significant variability in terms of FDG avidity. Even in the same patient, different lesions may have different degrees of FDG uptake. FDG metabolism and clearance occurs at a much faster rate in normal tissues than tumor tissue, and thus tumor-to-background ratios improves with time resulting in better lesion detection when imaging is delayed. Boerner et al. have shown that tumor-to-non-tumor and tumor-to-organ ratios were significantly higher for the images taken at 3 hours post-injection than for the 1.5-hour images, and lesion detectability was 83% in 1.5-hour images compared to 93% in 3-hour images in breast cancer patients. Although more delayed intervals between FDG injection and imaging might compromise image quality due to lower count rates, this is much less of an issue with an FDG sensitive probe. Longer intervals may accentuate the tumor to background ratios, and further improve FDG detection. Important contributors to the background radiation are the sites of physiologic FDG uptake. The in situ tumor to background ratios is strongly affected by the surrounding areas of physiologic uptake or accumulation. The brain uptake in the head and neck region, cardiac uptake in the chest, kidney uptake and the accumulation inside the bladder in abdomen and pelvis affect the in situ tumor to background ratios.

Gritters and colleagues (Gritters L S, Francis I R, Zasadny K R, Wahl R L. "Initial Assessment Of Positron Emission Tomography Using 2-Flourine-18-Flouro-2-Deoxy-D-Glucose In The Imaging Of Malignant Melanoma", *J Nucl Med,* 34, p 1420-1427 (1933)) found PET to be highly accurate for identifying cutaneous melanoma metastases. A number of other investigators have also found PET to be both sensitive and specific for metastatic melanoma. For distant metastases, numerous studies have shown PET to have equal or superior sensitivity to CT, MRI, and ultrasound (Schwimmer J, Essner R, Patel A, Jahan S A, Shepherd J E, Park K, Phelps M E, Czernin J, Gambhir SS. "A Review Of The Literature For Whole-Body FDG PET In The Management Of Patients With Melanoma", *Quarterly J Nucl Med,* 44, p 153-167, (2000); Finkelstein, SE, Carrasquillo J A, Hoffman J M, Galen B, Choyke P, White D E, Rosenberg S A, Sherry R M. "A Prospective Analysis Of Positron Emission Tomography And Conventional Imaging For Detection Of Stage IV Metastatic Melanoma In Patients Undergoing Metastasectomy", *Ann Surg Oncol,* 11, p 731-738 (2004); Kaleya R N, Heckman J T, Most M, Zager J S. "Lymphatic Mapping And Sentinel Node Biopsy: A Surgical Perspective", *Semin Nucl Med.* 35, p 129-134, (2005)). While melanoma is more likely to metastasize to the brain, lung, or liver, the pattern is unpredictable and so whole-body functional imaging is most suitable. Numerous studies have shown the value of PET in the management of patients with advanced melanoma, with treatment plan changing in 15-50% of cases (Gulec S A, Faries M B, Lee C C, Kirgan D, Glass C, Morton D L, Essner R. "The Role Of Fluorine-18 Deoxyglucose Positron Emission Tomography In The Management Of Patients With Metastatic Melanoma: Impact On Surgical Decision Making", *Clin Nucl Med,* 28, p 961-965 (2003); Damian D L, Fulham M J, Thompson E, Thompson J F. "Positron Emission Tomography In The Detection And Management Of Metastatic Melanoma", *Melanoma Res,* 6, p 325-329 (1996); Tyler D S, Onaitis M, Kherani A, Hata A, Nicholson E, Keogan M, Fisher S, Coleman E, Seigler H F. "Positron Emission Tomography Scanning In Malignant Melanoma—Clinical Utility In Patients With Stage III Disease", Cancer, 89, p 1019-1025 (2000); Jadvar H, Johnson D L, Segall G M. "The Effect Of Fluorine-18 Fluorodeoxyglucose Positron Emission Tomography On The Management Of Cutaneous Malignant Melanoma", *Clin Nucl Med*, 25, p 48-51 (2000; Stas M, Stroobants S, Dupont P, Gysen M, Van Hoe L, Garmyn M, Mortelmans L, De Wever I. "18-FDG PET Scan In The Staging Of Recurrent Melanoma: Additional Value And Therapeutic Impact", *Melanoma Res*, 12, p 479-490, (2002); Wong C S, Silverman D H, Seltzer M, Schiepers C, Ariannejad M, Gambhir S S, Phelps M E, Rao J, Valk P, Czernin J. "The Impact Of 2-Deoxy-2 [18F] Fluoro-D-Glucose Whole Body Positron Emission Tomography For Managing Patients With Melanoma: The Referring Physician's Perspective", *Mol Imaging Biol*, 4, p 185-190 (2002)). CT is, however, superior to PET in the detection of small pulmonary metastases, possibly due to respiratory motion (Gritters et al, ibid; Kumar et al, ibid; Rinne D, Baum R P, Hor G, Kaufmann R. "Primary Staging And Follow-Up Of High Risk Melanoma Patients With Whole-Body F-18-Fluorodeoxyglucose Positron Emission Tomography—Results Of A Prospective Study Of 100 Patients", *Cancer*, 82, p 1664-1671, (1998)). Neither lab tests nor imaging have been shown to be useful in detecting recurrence in asymptomatic patients. In patients with known recurrence PET has been shown to detect additional metastases and alter treatment planning. Stas et al. (Stas M, Stroobants S, Dupont P, Gysen M, Van Hoe L, Garmyn M, Mortelmans L, De Wever I. "18-FDG PET Scan In The Staging Of Recurrent Melanoma: Additional Value And Therapeutic Impact", *Melanoma Res*, 12, p 479-490 (2002) found the sensitivity, specificity, and accuracy of PET to be 85%, 90%, and 88%, respectively as compared to 81%, 87%, and 84% with conventional imaging. Fuster et al (Fuster D, Chiang S, Johnson G, Schuchter L M, Zhuang H M, Alavi A. "Is F-18-FDG PET More Accurate Than Standard Diagnostic Procedures In The Detection Of Suspected Recurrent Melanoma?" *J Nucl Med.* 45, p 1323-1327 (2004)) studied 156 patients with known or suspected recurrence and found the sensitivity, specificity, and accuracy of PET to be 74%, 86%, and 81% respectively compared to 58%, 45%, and 52% for conventional imaging.

FDG-PET imaging is becoming the method of choice for staging of breast cancer as well as for the detection of recurrent disease (Quon A, Gambhir SS. "FDG-PET And Beyond: Molecular Breast Cancer Imaging", *J Clin Oncol*, 23 p 1664-1673 (2005)), the location of metastases (Lonneux M, Borbath I, Berliere M, et al. "The Place Of Whole-Body PET FDG For The Diagnosis Of Distant Recurrence Of Breast Cancer", *Clin Positron Imaging*, 3, p 45-49 (2000)), and the monitoring of responses to radiation and chemotherapy. It is not yet widely used in primary diagnosis, though, due to significant variation in FDG avidity based on tissue pathology and tumor size (Luigi et al, ibid). Noninvasive breast cancer has been previously shown to be poorly imaged by FDG-PET (Wu D, Gambhir SS. "Positron Emission Tomography In Diagnosis And Management Of Invasive Breast Cancer: Current Status And Future Perspectives", *Clin Breast Cancer,* 4(Suppl 1), pS55-S63, (2003)) and the majority of FDG-PET research studies in the literature have been performed on patients with invasive breast cancer. There are significant variations between studies. The overall specificity of FDG-PET is relatively high, but false-positives do occur in some benign inflammatory conditions and fibroadenomas (Pelosi E, Messa C, Sironi S, et al. "Value Of Integrated PET/CT For Lesion Localization In Cancer Patients: A Comparative Study", *Eur J Nucl Med Mol Imaging*, 31, p 932-939 (2004); Avril N, Rose C A, Schelling M, et al. "Breast Imaging With Positron Emission Tomography And Fluorine-18 Fluorodeoxyglucose: Use And Limitations." *J Clin Oncol*, 18, p 3495-3502 (2000)).

Invasive breast cancer includes multiple histologic types including infiltrating ductal, infiltrating lobular, and combined infiltrating ductal and lobular carcinoma. Infiltrating ductal carcinoma has a higher level of FDG uptake and therefore is detected at a significantly higher sensitivity than infiltrating lobular breast cancer (Zhao S, Kuge, Y, Mochizuki T, Takahashi T, Nakada K, Sato M, Takei T, Tamaki N. "Biologic Correlates Of Intratumoral Heterogeneity In 18F-FDG Distribution With Regional Expression Of Glucose Transporters And Hexokinase-II In Experimental Tumor", *J Nucl Med*, 46, p 675-682 (2005); Amthauer H, Denecke T, Rau B, Hildenbrandt B, Hunerbein M, Ruf J, Scheider U, Gutberlet M, Schlar P M, Felix R, Wust P. "Response Prediction By FDG-PET After Neoadjuvant Radiochemotherapy And Combined Regional Hyperthemia Of Rectal Cancer: Correlation With Endorectal Ultrasound And Histopathology", *Eur J Nucl Med Mol Imaging*, 31, p 811-819 (2004)). This suggests that tumor aggressiveness is not the sole determinant of FDG uptake but that the mechanism of the variable FDG uptake by breast cancer cells is likely modulated by multiple factors including glucose transport-1 (GLUT 1) expression, hexokinase I (Hex-1) activity, tumor microvessel density, amount of necrosis, number of lymphocytes, tumor cell density, and mitotic activity index (Bos R, van Der Hoeven J J, van Der Wall E, et al. "Biologic Correlates Of [F18]Fluorodeoxyglucose Uptake In Human Breast Cancer Measured By Positron Emission Tomography", *J Clin Oncol*, 20, p 379-387, (2002)).

Image-guided core biopsy has the advantage of being the least invasive, most comfortable for the patient, and least costly method to determine the nature of image-detected abnormalities. The issue of a benign finding that apparently is not consistent with the clinical and radiographic findings has been most carefully studied in the management of breast abnormalities, which may be palpable or only observed by various imaging techniques. When a benign histologic diagnosis appears to be consistent with both the clinical findings and the radiographic features (the "triple test") the likelihood of missing malignant disease is minimized and follow-up examinations rather than surgical biopsy are recommended.

In the increasingly frequent scenario of pre-clinical, image-detected lesions, physical examination is not helpful in determining concordance; thereby leading to considerable uncertainty as to whether the area of interest has been appropriately sampled. Detecting radioactivity in the core sample obtained from a PET-positive abnormality would be a great advance in confirming accurate sampling, and therefore, definitive histologic diagnosis. The increasing sensitivity of imaging modalities, including magnetic resonance (MRI), computed tomography (CT), and positron emission tomography (PET) has resulted in the identification of abnormalities prior to the development of clinical manifestations. The nature of such abnormalities, which may represent primary tumors or metastatic lesions, must be determined. Minimally invasive, image-guided, core-needle biopsies are generally the first diagnostic approach. If a benign diagnosis is rendered, the clinician, in consultation with the radiologist and pathologist, must determine whether the finding is concordant with the clinical history and the configuration of the image-detected abnormality. Non-concordance implies the possibility of a sampling error, which often leads to a recommendation for open, surgical biopsy.

Examples of probes for intraoperative radiation detection which might be used in the procedures described herein include:

Scintillator-PMT systems, that use vacuum tube PMTs and scintillation crystals such as NaI(Tl), Scintillator-PIN diode systems that use PIN diodes as light detectors and then couple them to a scintillator with emissions around ~500 nm wavelength (such as CsI). The PIN diode has a gain of one (1) and therefore needs very low noise and high gain amplifiers, Cd—Te semiconductor detectors, that convert the energy from radiation directly to an electronic pulse, or Zn—Cd—Te semiconductor detectors that convert the energy from radiation directly to an electronic pulse.

Applicant's existing beta camera, developed in the early 1990s utilizes a position-sensitive photomultiplier tube (Hamamatsu 8520-00-12) that is optically coupled directly to a 1 mm thick sheet of plastic scintillator. A thin foil of aluminum Mylar (50 micron thick) is used to cover the front of the scintillator, to make it light-tight, while allowing positrons to enter the scintillator. This camera operates at 1200 Volts (F. Daghighian, P. Shenderov, B. Eshagian. "Interoperative Beta Cameras". *J. Nucl. Med.,* 446 (May 1995). Although the whole camera is well insulated electrically for ex-vivo use, to provide the level of insulation needed for its safe use in the surgical site is an impossible task. An improvement to the electrical safety was accomplished by building a flexible beta camera comprising a 2×1.5×150 cm$^3$ imaging grade array of optical fibers (each 100 microns thick) located between the sheet of plastic scintillator and the position sensitive PMT. The optical fibers act as an insulator, but light loss in this fiber bundle is large and degrades the sensitivity. A sub-millimeter resolution with a sensitivity of 4000 cps/microCi is achievable with this camera. Tornai et al. (M. P. Tornai, L. R. MacDonald, C. S. Levin, S. Siegel, E. J. Hoffman, "Design Considerations And Initial Performance Of A 1.2 Cm2 Beta Imaging Intra-Operative Probe." *IEEE Trans. Nuc. Sci.,* 43 (4), p 2326 (1996)) built a similar flexible beta camera and measured a line spread function of 0.5 mm for their 1.08 cm FOV camera, and a transmission image consisting of 0.5 mm holes 0.6 mm apart was successfully imaged. However, the sensitivity of this camera was not acceptable for surgical procedures. Yamamoto and colleagues built cameras with 10 and 20 mm diameters, and measured 0.8 mm and 0.5 mm FWHM, respectively (S. Yamamoto, C. Seki, K. Kashikura, H. Fujita, T. Matsuda, R. Ban, I. Kanno, "Development of a High Resolution Beta Camera for a Direct Measurement of Positron Distribution on Brain Surfaces." *IEEE Trans. Nuc. Sci.* 44 (4) p 1538 (1997)

Various solid state detectors have been proposed. Tornai and colleagues developed a prototype silicon strip detector, though this was never incorporated into a surgical device (M. P. Tornai, B. E. Patt, J. S. Iwanczyk, C. R. Tull, L. R. MacDonald, E. J. Hoffman, "A Novel Silicon Array Designed For Intraoperative Charged Particle Imaging." *Medical Physics,* 29 (11), p 2529 (2002)). Janacek et al. developed a positron-sensitive intravascular probe which incorporated a multi-element linear silicon array (M. Janacek, E. J. Hoffman, C. R. Tull, B. E. Patt, J. S. Iwanczyk, L. R. MacDonald, G. J. Maculewicz, V. Ghazarossian, H. W. Strauss, "Multi-Element Linear Array Of Silicon Detectors For Imaging Beta Emitting Compounds In The Coronary Arteries." *Proc. IEEE NSS/MIC* (2002). The disadvantage of silicon based beta cameras is that they do not have internal gain as does an SSPM, and they bring the electrical charge onto the surface of the beta camera. Therefore they are not electrically safe. A shortcoming of using CdTe or CdZnTe for constructing a beta camera is that they have high atomic numbers and high densities; therefore, they are more sensitive to unwanted background gamma rays than plastic scintillators (density of 1 and atomic number of 6).

Introduced in 2002, solid state photomultipliers have been used primarily in high energy and astrophysics experiments where very high sensitivity light detection is required (P. Buzhan, B. Dolgoshein, A. Ilyin, V. Kantserov, V. Kaplin, A. Karakash, A. Pleshko, E. Popova, S. Smirnov, Yu. Volkov, L. Filatov, S. Klemin, F. Kayumov, "The Advanced Study of Silicon Photomultiplier", *ICFA Instrumentation Bulletin,* 23 (Fall 2001); Buzhan P, Dolgoshein B, Filatov L et al. "Silicon Photomultiplier And Its Possible Applications", *Nuclear Instruments and Methods in Physics Research A,* 504 p 48-52 (2003). A silicon photomultiplier is a large assembly of avalanche photodiodes operating in Geiger mode. Each detector, which can be as small as 1 mm×1 mm, consists of an array of (~600) micropixels connected in parallel (FIG. 1)). The micropixels act individually as binary photon detectors, in that an interaction with a single photon causes a Geiger discharge. Each micropixel "switch" operates independently of the others, and the detector signal is the summed output of all micropixels within a given integration time. When coupled to a scintillator, such as by an optical glue, the SSPM detects the light produced in the scintillator by incident radiation, giving rise to a signal proportional to the energy of the radiation.

A recent development is a solid state or silicon photomultiplier (SSPM, or SiPM) developed by a team from the Moscow Engineering and Physics Institute (B Dolgoshein Int. Conf. on New Developments in Photodetection (Beaune, France) June 2002) together with Pulsar Enterprise in Moscow. The device comprises a large number of microphoton counters (1000/mm2) which are located on a common silicon substrate and have a common output load. Each photon counter is a small (20-30 μm square) pixel with a depletion region of about 2 μm. They are decoupled by polysilicon resistors and operate in a limited Geiger mode with a gain of approximately one million. This means that the SiPM is sensitive to a single photoelectron, with a very low noise level. Each photon counter operates digitally as a binary device. However the assembly of multiple SiPM is an analogue detector with the capability to measure light intensity within a dynamic range of about 1000/mm$^2$ and has high photon capability.

The photon detection efficiency of the SSPM is at about the same level as photomultiplier tubes (PMTs) in the blue region (20%), and is higher in the yellow-green region. The device has very good timing resolution (50 ps r.m.s. for one photoelectron) and shows good temperature stability. It is also insensitive to magnetic fields. These characteristics mean that the SSPM can be used in place of other known photodetectors (e.g., PMT, APD, HPD, VLPC). The main advantage of the SSPM is its small size (1×1 mm) and its low operating voltage of ~60 V. These characteristics render SSPM ideal for use in intraoperative and intra-luminal radiation detection probes and cameras.

One currently proposed medical applications for SSPM is in a small field of view PET scanner that can work in high magnetic fields of an MRI scanner (Rubashov, I. B., U.S. Pat. No. 6,946,841).

SUMMARY

The present invention is directed to instruments and instrumental techniques for locating radio-labeled sites which utilize a radiation detector for locating the position of the radiation tagged sites, for example in cancerous tumors or vulnerable plaque. Also described are unique new intraoperative radiation detection probes and cameras for use in these techniques. The instruments and instrumental techniques facilitate the surgical removal of labeled cancerous cells or plaque and the delivery of materials to treat the tumor or plaque to, for example, retard, stop or reduce the growth and spread of the cancer or plaque once the radiation labeled cancer cells or plaque is located.

BRIEF DESCRIPTION OF DRAWINGS

FIG. 1 is a schematic drawing showing a two dimensional array of SSPM assembled with a sheet of plastic scintillator.

FIG. 2 is a schematic drawing showing a single-detector module with a small plastic scintillator coupled to a SSPM for use in a beta probe or as an element of a beta camera.

FIG. 26 is an expanded schematic view of a probe embodiment that includes scintillators over the end and side of the probe tip.

DETAILED DISCUSSION

Breast Cancer Detection

Figure 3:
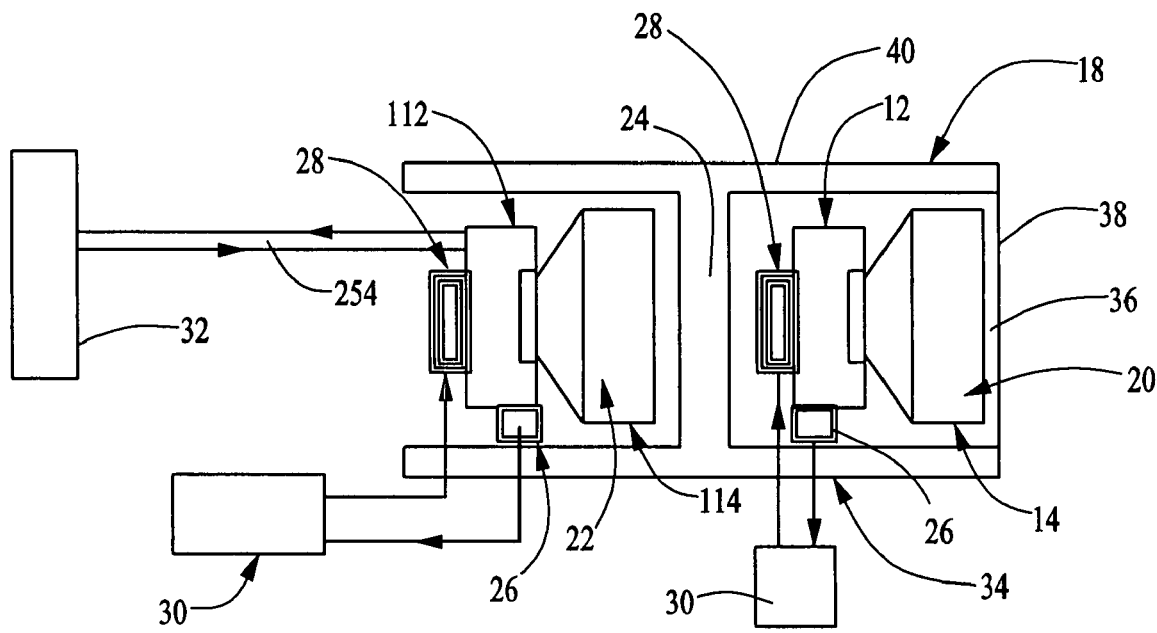
FIG. 3 is a schematic diagram of a dual-detector module for a beta probe or camera having a first detector and a second detector, the second detector for counting only the spurious gamma rays.

In 2005, there was an estimated 415,000 new cases of melanoma, breast, and colon cancers in the United States. Approximately 138,000 will ultimately develop metastases or have locally advanced disease. At least 10% should be eligible for surgical resection. If the probes (camera) can reduce the incidence of positive margins or subsequent local recurrence by 10-20%, then the incidence of re-operations could be reduced by 2,000-4,000 patients per year. Both the financial and emotional costs to patients would also be reduced.

Breast cancer usually recurs in the breast because the original primary tumor was not completely resected and the remaining cells were not destroyed by adjuvant radiation or systemic therapy. The accurate assessment of margins has assumed great importance in the conduct of lumpectomy. Various techniques have been used to assess margins postoperatively, including cytologic and histopathologic techniques. These techniques suffer from sampling problems and the fact that the results are delayed, requiring re-operation in approximately 20% of patients treated with lumpectomy. The ability to intraoperatively detect true involvement at the margins of resection within the lumpectomy bed would enable the surgeon to complete the successful lumpectomy by resecting all involved tissue in one operation. This would avoid a second operation in thousands of women annually and avoid recurrences in an unknown but probably large number. Numerous radioactive compounds for targeting and tagging particular body tissue and particularly different cancerous lesions are known in the art. Fluorine-18 deoxyglucose (FDG) has been particularly identified as having a high uptake in breast cancer tissue (Quon et al, ibid; Bos R, van Der Hoeven J J, van Der Wall E, et al. "Biologic Correlates Of [F18]Fluorodeoxyglucose Uptake In Human Breast Cancer Measured By Positron Emission Tomography'" *J Clin Oncol*, 20, p 379-387 (2002)). Positrons emitted from $^{18}$F in FDG can guide the beta probe to detect these residual tumor cells. Therefore the probe described herein and its use is of major importance in avoiding second operations and preventing recurrences in women with breast cancer who are undergoing breast-conserving therapy. An improvement of even 10 percent, that is, a >30-40 percent reduction in finding postoperative, cancer-positive margins, provides meaningful reduction in the re-operative rate for breast cancer patients across the nation.

An important objective of cancer surgery is to insure complete removal of all cancerous tissue. Tumor-positive margins dilute the benefits of surgery. Milligram deposits of cancer cells can be localized with a beta camera that can image the distribution of F-18 labeled fluorodeoxyglucose (FDG). However, the short (~1 mm) range of positrons in tissue requires the camera to be as close as possible to, and preferably in direct contact with, the open surgical field. Existing experimental beta cameras use high voltage detectors which are unsafe for in vivo use. The solution has been to use fiber optic coupling to keep the high voltage parts safely removed from the patient, but this approach significantly reduces sensitivity.

Set forth herein is a beta camera with the resolution and sensitivity to detect cancer deposits at least as small as 5 mg. Through the evaluation of various configurations of SSPMs and scintillators as shown and described herein, it has now been demonstrated that SSPMs have higher sensitivity than photomultiplier tubes and can operate at ~50 volts. They are also very small (1×1 mm). An absolute efficiency of at least 15% has been shown for a small plastic scintillator directly coupled to an SSPM as opposed to 0.2% for an identical scintillator coupled by fiber optics to a PMT. A first embodiment of beta camera, incorporating features of the invention, comprises a sheet of red plastic scintillator and a 2 dimensional array of SSPMs, including means to compensate for temperature variance ranging from 25 to 37° C.

The use of solid state photomultiplier (SSPM) which operates at very low voltages allows direct intraoperative use while performing at least as well as or better than prior art devices. Described herein are new beta cameras based on SSPM technology that surgeons can use to detect tumor margins with unprecedented sensitivity and in turn to reduce local relapse rates from the resected field.

Since 2002, solid state photomultipliers have been utilized in high energy physics laboratories. They have a gain of about 1 million, a working voltage of about 50 Volts, a size of about 1×1×0.5 mm and a low noise at ambient temperatures (20° to 40° C.). These properties were found to be favorable for constructing a intra-operative beta probe as set forth herein. Several variations of these detectors have been assembled into new devices for use in intraoperative procedures in the field of nuclear medicine.

Figure 21:
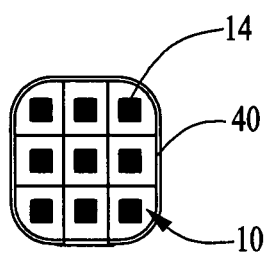
FIG. 21 is a top view of the mini-gamma imaging probe of FIG. 20 showing the nine detector modules.
Figure 20:
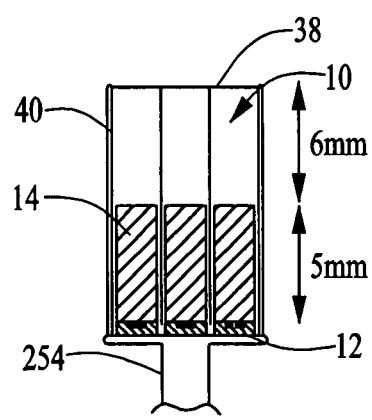
FIG. 20 is a side cut away view of a mini-gamma imaging probe with nine detector modules.
Figure 22:
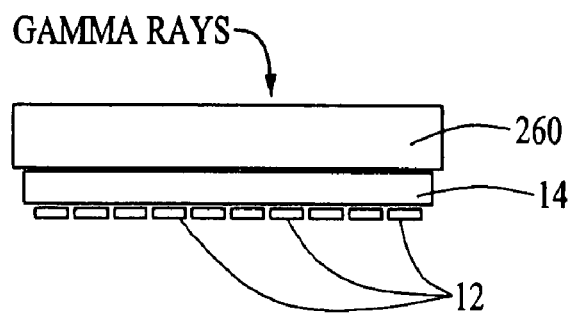
FIG. 22 is a second embodiment of a small gamma camera with a plate of scintillators coupled to an array of SSPM's.

A first embodiment of the SSPM beta camera incorporating features of the invention has a 10×10 array 10 of SSPM's 12 optically coupled to a plastic scintillator sheet 14 as shown schematically in FIG. 1. FIGS. 20 and 21 show a cutaway and end view of a probe including such an assembly. In a representative assembly, the size of each SSPM 12 is 2×2 mm and the size of the scintillator portion 14 is 20×20 mm. The unique advantage of such a probe is that by using an SSPM, a gamma probe is built with a typical dimension of 5 mm diameter and 10 mm long, that operates at a low voltage of 50 V and has a high sensitivity and gain. Each detector module is made by optically coupling a heavy scintillator, such as GSO, NaI(Tl) or BGO, to an SSPM. The total dimension of such a gamma imaging probe is 10×10 mm on the sides and about 12 mm long. This small size enables its use in laparoscopic and other endo-surgical applications or applied to the tip of surgical tools or mounted on the finger of the surgeon, for example, in the finger of the surgical glove. Each SSPM 12 is connected by a digital signal conduit (lead) 254 to its own electronic processors (not shown). Beta rays from a radiation source strike the scintillator generating scintillation light which is detected by the SSPMs which in turn generate a digital signal. The digital signals are used to generate an image on a screen 42, similar to Anger logic. The beta rays do not need a collimator since they have short ranges. FIG. 22 is a further embodiment of a small gamm camera including a plate of scintillators 14, such as bismuth germanate (BG0), GSO ($Gd_2S_1O_5$), or NaI(Tl) coupled to an array of SSPMs 12, which includes a collimator 260 for the gamma rays.

Gamma rays travel several centimeters in tissue; therefore a detector that is sensitive to gamma rays would be susceptible to spurious gamma rays emitted by distant organs and background tissue. This background radiation may obscure the tumor margins. One limitation of gamma probes in surgery or other medical procedures is their inability to distinguish between the signal and the background radioactivity which obscures the ability to localize small tumors with low tumor/background uptake ratios. On the other hand, beta rays travel only a couple of millimeters and so a beta detector senses only the local radioactive concentration. Beta sensitive probes 16, 18 shown in FIGS. 2 and 3, which incorporate features of the invention, can be used to detect radiation labeled tissue, particularly to detect FDG-avid cancer cells. In the single-detector beta probe module 16 shown in FIG. 2 a first plastic scintillator 14 connected to a SSPM 12 is used in the Beta detection assembly 20 to selectively detect beta over gamma rays. Although plastic scintillator 14 is selected to be relatively insensitive to gamma rays, it still detects some. These spurious gamma rays become significant when the background radioactivity is high. One way to avoid counting these spurious gamma rays is to raise the energy threshold of the detector and therefore loose some of the real beta count that results in low sensitivity. One remedy to this problem is the use of a reference gamma ray detector such as set forth in a dual-detector beta probe module that was proposed by the applicant in a prior patent (Mazziotta et al., U.S. Pat. No. 5,008,546). In this prior disclosed dual detector beta probe fiber optics were used to transmit the scintillation light to two PMTs which resulted in a significant loss of the level of the signal. That device also had the problem of asymmetric counting of the spurious gamma rays as a result of geometrical limitations that the fiberoptics placed on the design. Furthermore, optical fibers cause light-loss and therefore loss of signal. These problems are resolved in the dual-detector modules 18 disclosed in this application by the use of SSPM's and stacking the beta detector assembly 20 on top of a gamma detection assembly 22 which preserves symmetry (FIG. 3). The gamma detector assembly 22, comprising a scintillator 114 and a SSPM 112, which is also referred to as a reference detector, placed behind the beta detection assembly 20 detects only the gamma rays because a 1 mm thick aluminum plate 24 is placed on the exposed surface thereof to shield the beta rays from reaching the detector in the shielded area. In the system electronics 32, counts from this reference detector 22 are subtracted from those of the beta detector 20 to determine the pure beta count rate. Both the beta detector assembly 20 and the reference detector, as discussed below, can also include a temperature sensor 26 and a cooling or heat source 28, such as a Peltier cooler, and a control circuit 30 to maintain a fixed standard temperature. A circumferential metal shield 40 may also be included so that beta rays do not enter the gamma detector from the side. This beta probe is ideal for the detection of minute tumor remnants which, due to the short penetration range of beta rays in tissue, are not obscured by the radioactivity accumulated in normal tissues.

Figure 25:
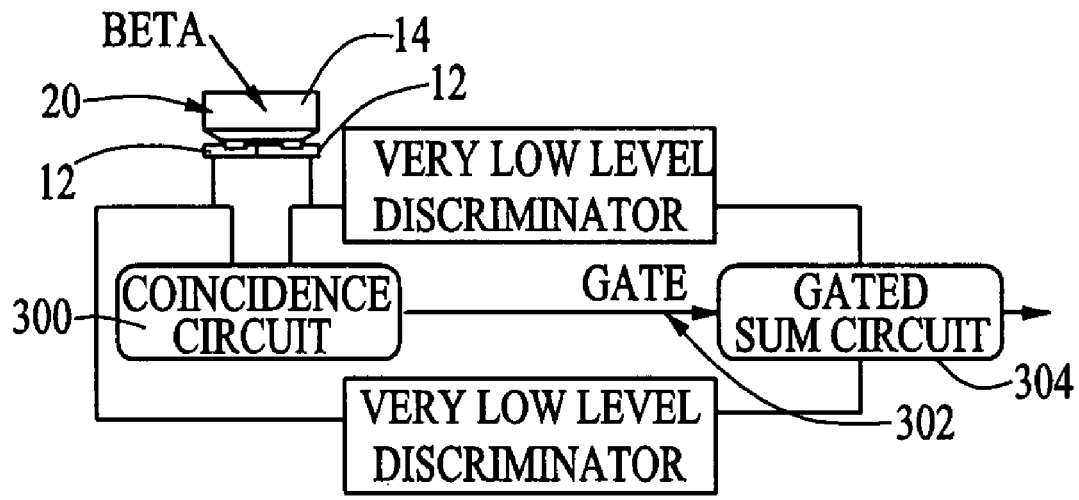
FIG. 25 is a schematic diagram of a coincidence circuit used to sum the signals from the two beta detectors (SSPMs) shown in FIG. 24.
Figure 24:
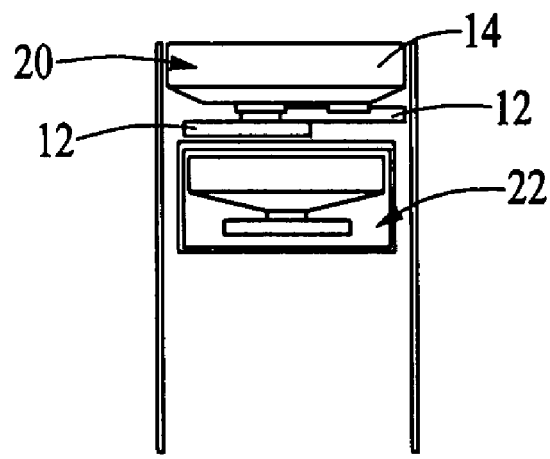
FIG. 24 is a modification of the dual detector module of FIG. 3, including two SSPM's collecting the signals generated by beta rays in a single scintillator.

Further, because each individual Beta detector 20 has its own independent electronic noise pattern, low-energy beta rays may generate signals that are smaller than the electronic noise. Energy thresholding above the electronic noise level can cause these low-energy betas to be ignored. Therefore it is important that procedures be undertaken to eliminate or hide the detector electronic noise or to amplify the beta probe output. In order to count the low energy beta rays using a beta probe and increase its sensitivity, the design of FIG. 3 is modified to have two SSPMs 12 such as shown in FIG. 24. The beta rays incident on the beta detector 20 generate light in the scintillator 14 which is counted by the two SSPMs simultaneously. As shown in FIG. 25 a coincidence circuit 300 is used to open the gate 302 of a summing circuit 304. The discriminator levels are set below the highest electronic noise levels, to reduce the electronic noises but not eliminate them completely. If the noise pulses of the two SSPM detectors do not happen in coincidence, the gate will stay closed and no event will be counted. On the other hand, if there is a low scintillation light burst due to a low energy beta ray hitting the scintillator, then both SSPM detectors will generate signals in coincidence. The gate will open, and the summed pulses indicate the existence of real scintillation signals, and they are counted. This technique of coincidence-noise-reduction allows the energy threshold on each one of the detectors to be lower and the low energy beta counts that previously would have been below the energy threshold, and consequently not counted, are now countable.

Figure 8:
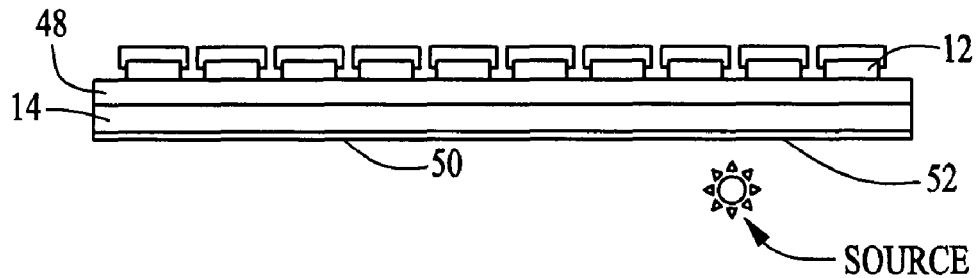
FIG. 8 is a schematic drawing of a first embodiment of a scintillator/SSPM assembly for use in the assembly of FIG. 1 or FIG. 7.
Figure 9:
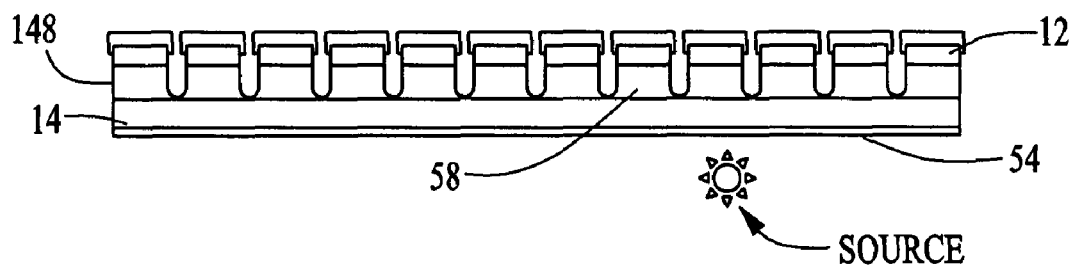
FIG. 9 is a schematic drawing of a second embodiment of a scintillator/SSPM assembly for use in the assembly of FIG. 1 or FIG. 7.
Figure 10:
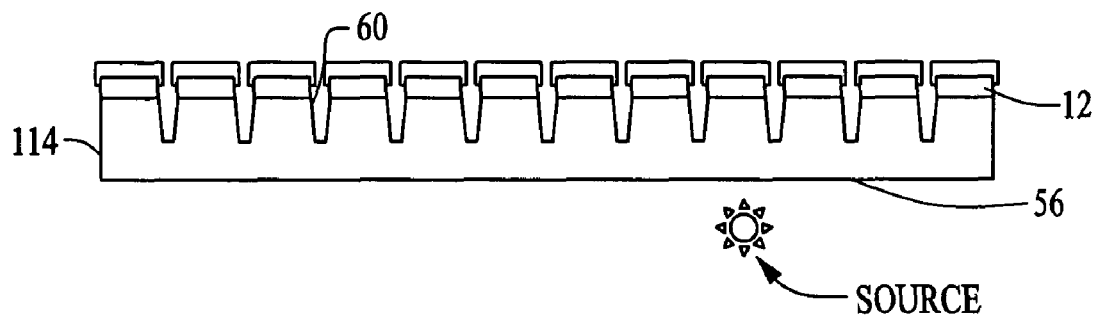
FIG. 10 is a schematic drawing of a third embodiment of a scintillator/SSPM assembly for use in the assembly of FIG. 1 or FIG. 7.

This method of coincidence noise reduction and increase in the sensitivity is implemented in the dual detector beta probe as shown schematically in FIG. 24, where the first and second SSPM 12 are partially staggered to allow packing in a 5 mm diameter tube. A third "reference gamma detector" 22 is also used as discussed herein above. In a beta camera such as shown in FIGS. 8, 9, and 10 one or more adjacent detectors can be paired to achieve coincidence noise reduction and increase the sensitivity. As a result a probe can be built to detect the presence of beta radiation or low energy gamma radiation emitted from labeled sites in the human body comprising a scintillator coupled to two or more solid state photomultipliers. Signals generated by the photomultipliers are fed into a coincidence circuit that delivers a signal only if the two signals fed thereto are within a pre-set time window, said delivered signal being used to trigger counting of the signals of one or more of the solid state photomultipliers and prevent the electronic noise pulses from being counted as beta rays.

FIG. 26 shows an embodiment incorporating features of the invention which comprises a probe 310 in which the tip 312 of the probe 310 as well as about 0.5 inches of the length of the lateral side 314 of the probe's cylindrical surface adjacent the tip 312 is covered by SSPM light detectors 12. These light detectors 12 are optically connected to two plastic scintillator pieces, namely a cylindrical collar 316 and a tip cover 318. A sheet of BC-430 scintillator (Saint-Gobain Crystals, Newbury, Ohio), wrapped in 2 layers of Teflon tape on the sides and top was used. This probe 310 uses "solid state photomultipliers" or "Silicon Photomultipliers" 12 for detection of scintillation light. The signals are digitized using multiple LabView-conrolled 8-channel data acquisition boards, and then are used to generate an image.

Figure 27:
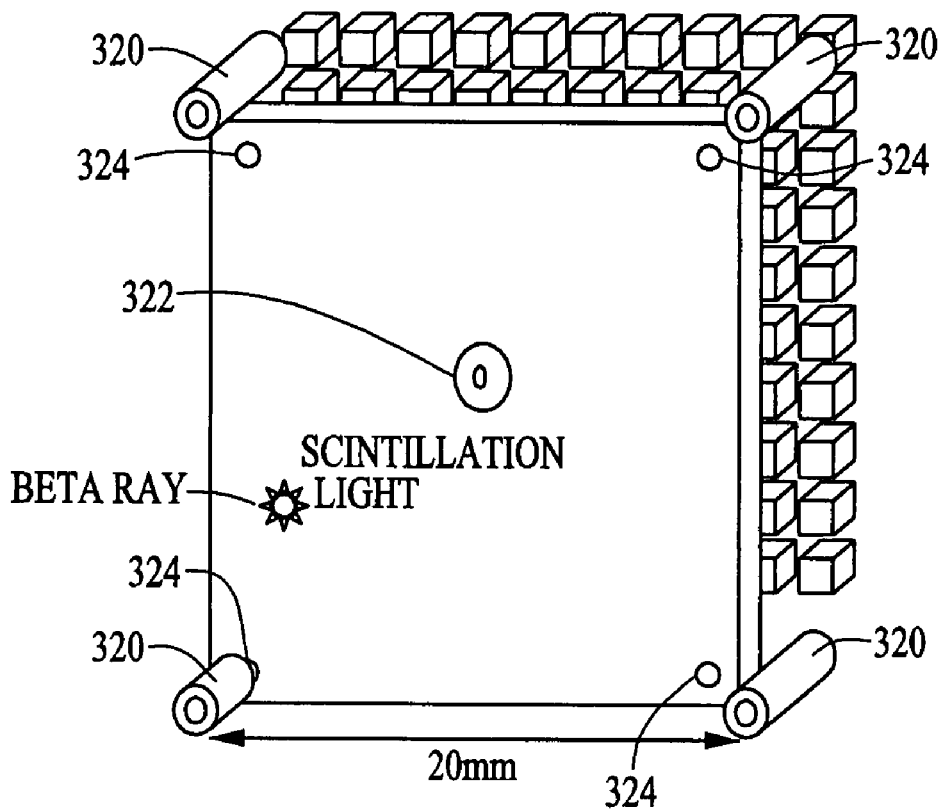
FIG. 27 is a variation of the array assembly of FIG. 1 including suction ports, position marking devices and a digital imaging camera.

For accurate beta ray measurements and imaging, it is preferred that the detector be brought into direct contact with the tissue under investigation and stay stationary with respect to tissue during the image acquisition period. The proposed device provides this capability. To assist in obtaining good contact with the tissue surface and stay fixed, suction can be applied to the tissue surface through or around the probe. FIG. 27, a modification of FIG. 1, shows one such device where multiple suction holes or tubes 320 are placed on the surface of the camera. The operator has the option to control the negative pressures and turn the vacuum on and off at each of these holes.

The beta camera of FIG. 27 also includes a centrally located visible-light digital camera 322 within the array of SSPM's and the scintillator so that a digital photograph of the tissue and the radioactive image can be superimposed. The system also includes a position marking device 324, preferable mounted within or adjacent the suction tubes 320. Examples of suitable marking devices are a laser beam marker or an inkjet dispenser. Technology such as used on inkjet printers can be incorporated within the probe tip. Inkjet technology uses a Piezoelectric crystal at the rear of the ink reservoir. This crystal flexes when an electric current is applied to it. To place a marking dot on the tissue being imaged, a current is applied to the Piezo element which then flexes and, in so doing, forces a drop of ink out of the nozzle on to the adjacent tissue. Preferred colors are blue, green or black but other colors readily imaged on the tissue, which is red in color, can be suitable.

A visual image of the surgical field can be acquired by lifting the beta camera off of the tissue surface, for example by about 0.5 inch. A flash of light is used to brighten the field and the four corners of the field of view which have been marked by a laser or ink spots. A beta ray image of the field is also generated and the visual image and the beta ray image can be digitally stored and displayed on the same screen. A software program within the image receiving electronics uses the laser or ink spot to automatically superimposes the corners of the beta image with the visual image.

Further, it is important that the radioactive tissue with higher uptake, or hot spot, once located, be marked. In prior devices, after observing a hot-spot on the image screen, the corresponding location on tissue could not be accurately found after the camera was removed from the tissue surface. This is particularly critical in endo-surgical applications of the beta camera. A marking mechanism described herein used in conjunction with the devices described addresses this major deficiency of the prior art.

Figure 4:
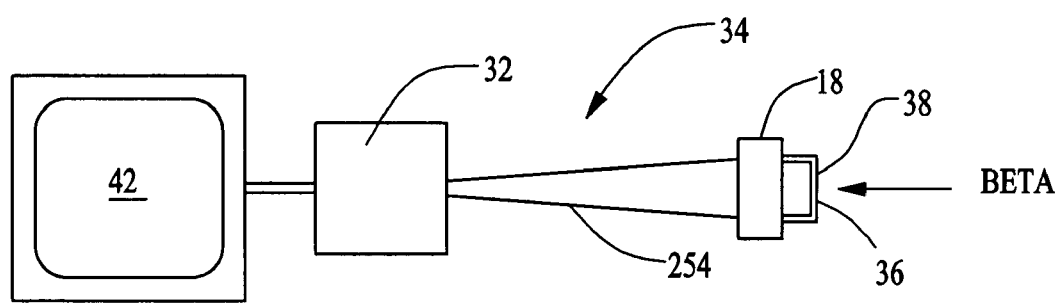
FIG. 4 is perspective drawing schematically showing a beta camera which can include the two-dimensional array of single-detectors of FIG. 2 or the dual-detectors of FIG. 3.

FIG. 4 is a schematic diagram of a beta ray camera 34 incorporating the SSPM and a scintillator film assembly as shown in FIG. 2 or FIG. 3. The beta camera 34 is shown to include the dual detector module 18 of FIG. 3, the signal processing electronics 32 and a display screen 36 to provide a visual display of the beta counts detected. To meet the UL electrical safety requirements for surgical instruments, novel arrays of solid-state photomultipliers (SSPM, Photonique SA, Geneva, Switzerland), that operate at 50 Volts have been utilized in the probes described herein. A thin stainless steel foil 34 (5 microns thick obtained from Goodfellow Inc., Devon, Pa.) is wrapped around the circumference of the assembly to prevent ambient light from entering the camera and interfering with positrons entering through the contact end 36 of the scintillator 14. Software provided in a data processing unit 32 generates uniformity look-up tables and other corrections necessary to enable the data generated by the camera 34 to process and display the images on the display 36. The device satisfies the U.S. and international standards IEC60601-1, EN60601-1, UL2601-1, CSA C22.2 No. 601.1 for surgical instruments. The scintillator 14 of choice for the selective detection of beta rays over gamma rays is a plastic scintillator, due to its low atomic number which reduces its sensitivity to background gamma rays. Each SSPM is coupled to a piece of Bicron BC-430 plastic scintillator. The SSPM 12 is also mounted on a ceramic substrate and has compact dimensions of 3×3 mm and 1 mm thickness. The scintillator, as shown in FIGS. 2 and 3, is machined to have a truncated base maximizing the light transmission to the sensor. A 5 micron thick stainless steel foil may be shaped into a cap and glued to the ceramic base of the SSPM using bio-safe glue. This foil also acts as a reflector of scintillation light.

Figure 5:
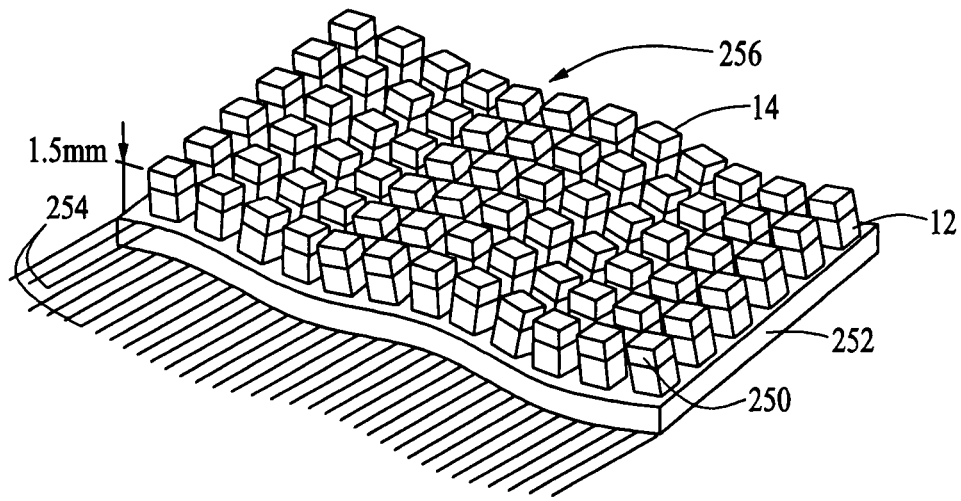
FIG. 5 is a schematic drawing of a two-dimensional array of SSPM/scintillator modules on a flexible membrane.

In a second method, instead of using a single sheet of plastic scintillator coupled to multiple SSPM's, each SSPM 12 is coupled to its own scintillator 14 to form a SSPM/scintillator module 250. The multiple SSPM/scintillator modules 250 are mounted on a flexible membrane 252 and the leads 254 from each module 250 is fed through the membrane 252 to the system electronics 32. This flexible-detector arrangement 256 is shown in FIG. 5. These modules can then be packed in one dimensional or two dimensional arrays to form a beta camera or molded to different shapes such as a trough or the surface of a tube.

Gamma rays travel several centimeters in tissue. Therefore a detector that is sensitive to gamma rays is susceptible to spurious gamma rays emitted by distant organs and background tissue. This background radiation may obscure the tumor margins. On the other hand, beta rays travel only a couple of millimeters and therefore a beta detector senses only the radioactive concentration adjacent to the contact end 36 of the camera 34. All positron-emitting radioisotopes emit beta (the positrons are a form of beta rays) as well as 511 keV gamma rays. Therefore in order to detect a small superficial tumor, a beta detector should be used. Further, since beta rays travel only a very short distance in solids, it is preferred that the detector and the tissue should come in contact with each other. A thin membrane 38 is preferably provided to separate the detector from the tissue. Also, the detector operates under low voltages in order to ensure electrical safety.

Positron emitting isotopes, for example F-18, are used for PET scanning. In tissue, positrons emitted from the F-18 containing compounds travel a couple of millimeters before they convert to high-energy gamma rays of 511-keV energy.

Prostate Cancer Detection

It is estimated that in 2005, approximately 232,090 men in the United States were diagnosed with prostate cancer and 30,350 men died from the disease. Within the next 15 years, prostate cancer is predicted to be the most common cancer in men. Annually, surgical treatment is offered to over 70,000 men. Radical prostatectomy is considered the gold standard of treatment for clinically localized prostate cancer. This involves removal of the prostate, seminal vesicles, surrounding fascia and often regional lymph nodes.

While surgery is safe, it is often associated with postoperative impotence and some times residual cancer around the nerves (positive margins). This is due to the close proximity of nerves, poor differentiation from surrounding tissue and the lack of clear planes of demarcation between nerves and cancerous tissue. The goal of prostate cancer surgery is to remove the cancer harboring prostate gland with minimal damage to the surrounding structures (i.e. nerves for erection and continence). These two goals are mutually competing as nerves for erection often travel very close to the prostate enclosed within layers of tissue. Not only are the nerves almost hugging the prostate, they are very tiny and often invisible to the unaided eye because of obstruction. This technical challenge sometimes results in either incomplete removal of the cancer with positive surgical margins near the nerves or postoperative impotence due to the damage or excision of these nerves.

The incidence of positive surgical margins in patients who have RRP for clinically localized prostate cancer has ranged from 14% to 46%. Cancer in the surgical margin has been shown to be a significant independent adverse factor associated with a greater risk of biochemical disease recurrence, local disease recurrence in the prostatic fossa, and systemic progression with death from prostate cancer.

The diagnosis of positive margins is usually made postoperatively by the pathologist when a tumor is detected at the surgical resection surface. To date there is no method by which tumor cells can be detected by visual inspection. Intraoperative visualization of cancer cells during radical prostatectomy would result in precise delineation of boundaries of malignancy and have far reaching implications in other surgical specialties.

An important objective of cancer surgery is to insure complete removal of all cancerous tissue. Further, tumor-positive margins dilute the benefits of surgery. To address these issues a monoclonal antibody that specifically binds to an external epitope of the prostate specific membrane antigen $PSMA_{ext1}$ (such as monoclonal antibody J591) has been produced and labeled with radioactive isotopes In-111. Lu-177 and Y-90. When injected into the patient it migrates to the tumor cells in the prostate as well as the surrounding tissue if the cancer has spread.

J591 is an anti-PSMA mAb that binds with 1-nM affinity to the extracellular domain of PSMA. Murine J591 antibody has been deimmunized using a method involving specific deletion of human B- and T-cell recognized epitopes. In vitro and animal studies of radiolabeled J591 has demonstrated the superiority of radiometals Yttrium-90 (90Y) and Lutetium-177 (177Lu), presumably due to their longer intracellular half-life ($t_{1/2}$), as compared with the rapid dehalogenation and washout of 131I-J591. The 90Y and 177Lu, both beta emitters, have very different physical properties. The 90Y has a shorter half life (2.7 vs 6.7 days), a higher energy (max, 2.3 v 0.5 MeV), and a longer range (max, 12.0 v 2.2 mm) than 177Lu. As a pure beta emitter, 90Y cannot be used for imaging and requires the use of 111Indium as a surrogate label for scintigraphy and dosimetry calculations. In contrast, 177Lu emits 15% of its energy as a gamma emission in addition to the beta emissions, and can be imaged directly using a gamma camera. Bander et al. elected to evaluate both 90Y- and 177Lu-J591 in two independent phase I clinical trials. As to the phase I dose escalation trial of 177Lu-J591 in patients with progressing androgen-independent PC it was found that among the 35 patients receiving 177Lu-J591, 30 (86%) had metastatic disease detected on screening imaging studies. Specifically, 21 (60%) patients had bone-only metastases, six (17%) had soft tissue-only metastases, and three (9%) had both bone and soft tissue disease. In all of these 30 patients, all known sites of metastatic disease were successfully imaged by 177Lu-J591 scintigraphy. One patient with bone metastases had many more lesions visible on antibody scan than on bone scan. Another patient with a negative bone scan had a positive antibody scan that was confirmed positive by MRI. The bone scan of both patients later converted to positive in sites presaged by their antibody scans Gamma and beta cameras incorporating the invention described herein were used for detection of the cancer tissue in the prostate, which has high uptake of the radioactive labeled J591 Mab. Very small deposits of cancer cells in the margin of the resected prostate can be localized with the beta camera designed to image the distribution of the Lu-177 labeled J591 Mab. In addition, gamma rays from lymph nodes that are infected by cancer can be detected by the small gamma imaging probe or gamma camera of this invention.

Pelvic lymphadenectomy (PLND) provides important information on tumor stage and prognosis that can not be matched by any other procedures to date. However, consensus has not been reached concerning the indication for, nor the extent of pelvic lymphadenectomy needed for exact staging of prostate cancer. The presence of lymphatic metastases markedly increases the risk of progression to metastatic disease and death. PLND may thus have a therapeutic benefit rather than solely being a diagnostic procedure.

Currently used preoperative nomograms such as the Partin tables are inadequate to accurately predict occult pelvic lymph node disease. Imaging techniques such as CT scan, MRI and PET scan have not proven beneficial in identifying smaller pelvic nodes. (<5 mm) in which metastasis are predominantly found in prostate cancer. PLND, however, can add to the morbidity of any surgical procedure. Complications associated with lymph node dissection are lymphoceles, lymphedema, venous thrombosis and pulmonary embolism. An accurate intraoperative tool for visualizing micrometastasis would allow identification of patients with nodal involvement who would benefit from a PLND. A gamma probe or small gamma camera that is small enough to be incorporated into a laparoscopic or robotic surgical setting, such as the assemblies described in this invention, help in these types of cases as well as the detection of cancerous lymph nodes.

The inherent morbidity associated with conventional open radical prostatectomy has led to the search for less invasive options. One of these options is robotic radical prostatectomy. This specialized surgery for prostate cancer has been developed in the last 5 years. More than 18,000 robotic prostatectomies were performed in 2005 alone. This procedure uses a state of-the-art daVinci™ surgical system, through which the surgeon uses a three-dimensional computer vision system to manipulate robotic arms. These robotic arms hold special surgical instruments that are introduced into the abdomen through tiny incisions. A stereoscopic camera—a long, thin, lighted telescope—is inserted and connected to the computer monitor that allows the surgeon to see inside the body. The vision is stereoscopic and magnifies the three-dimensional anatomy. The stereoscopic magnification helps the surgeon find the delicate nerves and muscles surrounding the prostate. The depth perception allows precision during the surgery and helps in meticulous surgical dissection. The magnification is 10- to 15-fold and the prostate and its surrounding structures are visible through a clear illuminated camera. Every structure is identified and precisely separated from prostate. This small camera can be negotiated into very narrow corners of the body that may normally be invisible to the surgeon when looking directly inside the body. The robotic arms can rotate a full 360 degrees allowing the surgeon to manipulate surgical instruments with greater precision and flexibility.

These instruments are mounted at the tip and thus can be controlled with high fidelity and dexterity. This ability to move small instruments in any possible direction helps tremendously in performing delicate surgical moves which involve the ability to rotate, turn, flex, extend, push, twist, abduct and adduct while performing complex surgical tasks. An embodiment of the current beta camera invention having a width less than 12 mm allows its entrance through the port on a laparoscope and can be used in robotic procedures, such as prostectetomy surgeries, for detection of margins. Also, a gamma probe or camera described herein can be inserted to detect cancerous metastasis, for example, in lymph nodes.

Surgery is an important mode of treatment of prostate cancer. However, the following problems remain:

Complete local resection of cancerous tissue is not possible in some cases since normal and prostate cancer tissues are not visually distinguishable. In approximately 30% of cases the margins of resection are involved (or positive). Unfortunately, this finding is currently made by the pathologist from the resected prostate, well after the surgery, when there is little that can be done to rectify the situation.

Assessment of lymph nodes is important in staging the cancer. This is done by multiple node dissections and pathological evaluations in the vast majority of patients, which results in increased morbidity, operative time, and cost.

Currently, trans-rectal biopsies, in post-prostatectomy patients with elevated PSA, are done with ultrasound guidance. However, often no suspicious lesion is seen and biopsies are little more than random samples. As a result, there is a low sensitivity rate.

As a feature of the invention described herein applicant addresses these problems by using a monoclonal antibody (such as J591) which has been produced and labeled with radioactive isotopes In-111, Lu-177 and Y-90. J 591 specifically binds to an external epitope of the prostate specific membrane antigen $PSMA_{ext1}$. Gamma and beta cameras described herein are used for the detection of cancer tissue that has high uptake of the radioactive labeled J591 Mab.

An important objective of prostate surgery is to insure complete removal of all cancerous tissue. Tumor-positive margins dilute the benefits of surgery. Very small deposits of cancer cells, such as 1 mg in size, can be localized with a beta camera that can image the distribution of Lu-177 labeled J591 Mab. However, the short (~1 mm) range of beta rays in tissue requires the camera to be as close as possible to, and preferably in direct contact with the open surgical field. Existing experimental beta cameras use high voltage detectors, which are unsafe for in vivo use. A prior approach has been to use fiber optic coupling to keep the high voltage parts safely removed from the patient, but this approach reduces sensitivity significantly.

Applicant utilizes a solid state photomultiplier (SSPM) assembly described above to solve this problem. The SSPM operates at very low voltages and yet performs as well as conventional devices, and allows direct intraoperative use. Applicant has developed a new beta camera based on SSPM technology that surgeons can use in detecting tumor margins with unprecedented sensitivity, providing the potential to reduce local relapse rates from the resected field.

The beta probe 16, and particularly the beta probe with reference detector 18, is particularly sensitive to short-range positrons emitted by FDG and therefore it is highly sensitive to minute amounts of cancer cells that may be located within a millimeter of the surgical margin and effective in detecting small amounts of tumor at the margin of resection. As shown in FIG. 3, the dual detector beta probe 18 comprises two detectors, a first detector 20 that detects (counts) both positrons and gamma rays and a second detector 22 that detects (counts) only gamma rays. These counts are then transmitted to first and second SSPMs 12. Because gamma rays travel several centimeters in tissue, both detectors register counts emanating from distant tissues and not solely from the tissue under examination. Using electronic or software techniques the counts of the second detector 22 are subtracted from the counts from the first detector 20 so that only the counts generated by the positrons remain. Because positrons can travel only a couple of millimeters, this corrected count is an indication of local concentration of FDG. Counts, updated each second, are then passed through a data processor 32 where they are electronically processed and displayed on a visual screen or monitor 42 so that the surgeon can identify, isolate and remove the labeled cells.

The beta probe described herein circumvents this limitation of traditional gamma probe technology. Many radioisotopes used in nuclear medicine emit electrons or positrons. Since beta rays have short depth of penetration in tissue (~1 mm), a beta sensitive probe is not affected by the background gamma radiation.

The beta camera 34 described herein which can be hand held or built into a probe or catheter provides real time imaging of positron emissions. This beta camera 34 is capable of providing an image of the radioactive concentrations near the surface of the surgical field as well as ex-vivo imaging of resected tumors, for locating cancer on the margins. Scanning the surgical field with prior available probes can result in minute quantities of cancerous tissues being missed. The intra-operative beta camera 34 described herein provides an image of the surgical field as well as enables the surgeon to detect any focal concentration of radioactivity. Detection of minute cancer remnants on or near the surface of the surgical field is less time-consuming with this beta camera than with prior beta probes, and is more reliable in surveying the entire resected tumor bed. Real-time imaging of beta emitting tumor tracers alleviates many uncertainties that presently exist in cancer surgery.

SSPMs have many advantages over photomultiplier tubes, the current standard for scintillation-based detection of radiation. Perhaps most importantly, the operating voltage for SSPMs is around 50 V, as opposed to the kilovoltages required for PMTs, and therefore SSPMs have superior electrical safety when used inside the body. SSPMs are also extremely small. A 1×1 $mm^2$ detector performs comparably to a PMT with a 1 cm diameter and 5 cm length. SSPMs demonstrate extremely fast signal rise time (~40 ps), high gain (~$10^7$), good quantum efficiency at 450 nm (>20%), high stability, and low noise at room temperature. They are also completely insensitive to magnetic fields encountered in medical environments.

Figure 6:
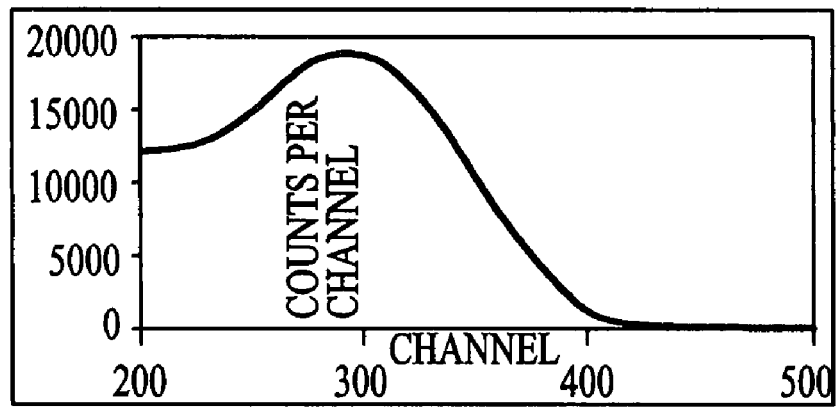
FIG. 6 is a graph showing the energy spectrum of the beta rays from an F-18 isotope received by a particular single-detector SSPM assembly with a plastic scintillator.

A set of SSPMs (SSPM-050701GR) obtained from Photonique Inc. (Geneva, Switzerland) had a sensitive area of 1×1 mm and overall size of 3×3 mm. A 2×2 mm device is also available. The best quantum efficiency of these SSPM is in the green region of the spectrum. Therefore, a green plastic scintillator sheet, obtained from Saint Gaubain Inc., was coupled to the SSPM using optical grease. A positron source of F-18 placed next to the scintillator, using a bias voltage of 51 Volts, produced the energy spectrum shown in FIG. 6. The sensitivity of this configuration was compared with the conventional method of using a 5 mm long plastic scintillator coupled to a 400 mm long clear optical fiber to connect the plastic scintillator to a PMT. The prior devices used the optical fiber to provide electrical isolation and safety between the tissue and 1200 vols that is present in the PMT. The plastic scintillator was sheathed using a five micron thick stainless steel foil. A point source of F-18 was made by soaking a 1 mm piece of tissue paper soaked with a solution of F-18 FDG, dried and sandwiched between two layers of Scotch tape placed in a well. Measurement of the counts from that sample was made using each assembly and compared using a dose calibrator of 10 microCi. When the plastic scintillator was brought into contact with the test source 50,000 counts per second were measured using the SSPM, yielding a sensitivity of 5000 counts/sec for 1 microCi of activity. The value obtained for the optical fiber-PMT configuration was 100 cts/s/microCi. This experiment demonstrate that SSPM assembly described herein is superior to PMT-optical fiber configuration for detection of beta emitting radiotracers in vivo. Additionally, a uniformity correction can be built into the device by acquiring an image of a flat source over an extended acquisition time and using the information obtained to generate a look-up table for uniformity correction of future acquired images.

Figure 7:
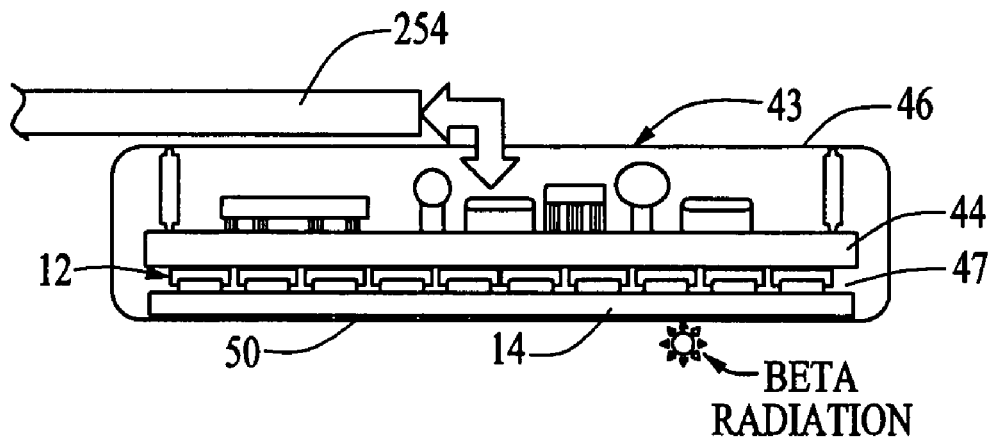
FIG. 7 is a schematic drawing of a further embodiment of an assembly having a sheet of plastic scintillators coupled to a one-dimensional or two-dimensional array of SSPMs.

FIG. 7 is a schematic of a further embodiment of a detector assembly 43 having the scintillator 14 coupled to an array of SSPM 12 with an electronic circuit board 44 mounted to the SSPMs 12. The assembly is enclosed in a capsule 46 formed from 5 micron thick stainless steel foil forming a barrier encasing the plastic scintillator and array of solid state or silicon photomultipliers on its front, rear and side surfaces. The foil is mechanically strong and enables the camera to be cleaned as well as gas sterilized. Three variations 52, 54, 56 of the scintillator/SSPM portion 47 of FIG. 7 are shown in FIGS. 8, 9 and 10. The first variation 52 of the scintillator/SSPM portion 47 shown in FIG. 8 is substantially the same variation as incorporated in the assembly of FIG. 7. FIG. 8 shows a flat scintillator sheet 14 with a plastic light guide 48 between the scintillator sheet 14 and the SSPMs 12, the plastic light guide 48 having approximately the same dimensions as the scintillator 14. A thin stainless steel membrane 50, which is a part of the stainless steel capsule 46, is shown covering the lower surface of the scintillator 14. The thinner stainless steel membrane 50 allows transmission and detection of the beta radiation while the thicker barrier material on the rear and side surfaces acts as a barrier to light and radiation (beta radiation) providing preferential beta radiation transmission to the front surface of the scintillator 14. FIG. 9 shows a flat scintillator sheet 14 with the light guide 148 having a first surface in contact with, and of substantially the same dimension as the scintillator 14. The opposite surface has multiple tapered portions 58, each being connected to an SSPM 12, to direct maximum scintillation light to the individual SSPMs 12. FIG. 10 utilizes a scintillator sheet 114 with discrete tapered zones 60 which taper down toward the attached SSPM. In this instance the individual SSPMs 12 are each attached directly to the end of one of the discrete tapered zones 60 of the scintillator 14. Referring to FIG. 7, the output from each of the SSPM in each of the variations 52, 54, 56 of FIGS. 8-10 is feed to the electronic circuit board 44 attached thereto for further processing and display.

Following are several tests performed using a beta probe as described therein. A disposable pre-sterilized plastic camera drape (which may be used in some surgical procedures) was not used since it attenuates the beta rays of F-18 by 30%.

Example 1

Figure 11:
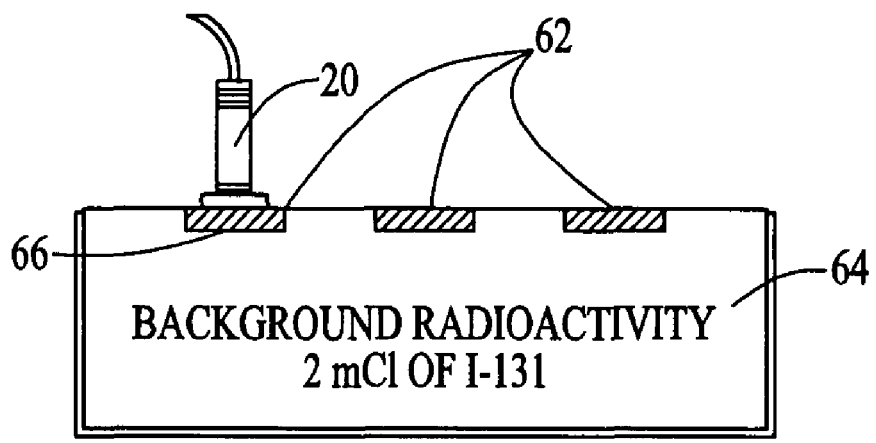
FIG. 11 is a schematic representation of a test apparatus used to determine the capability of a beta probe or camera incorporating features of the invention to detect and record the level of radiation emitted from simulated tumors.
Figure 12:
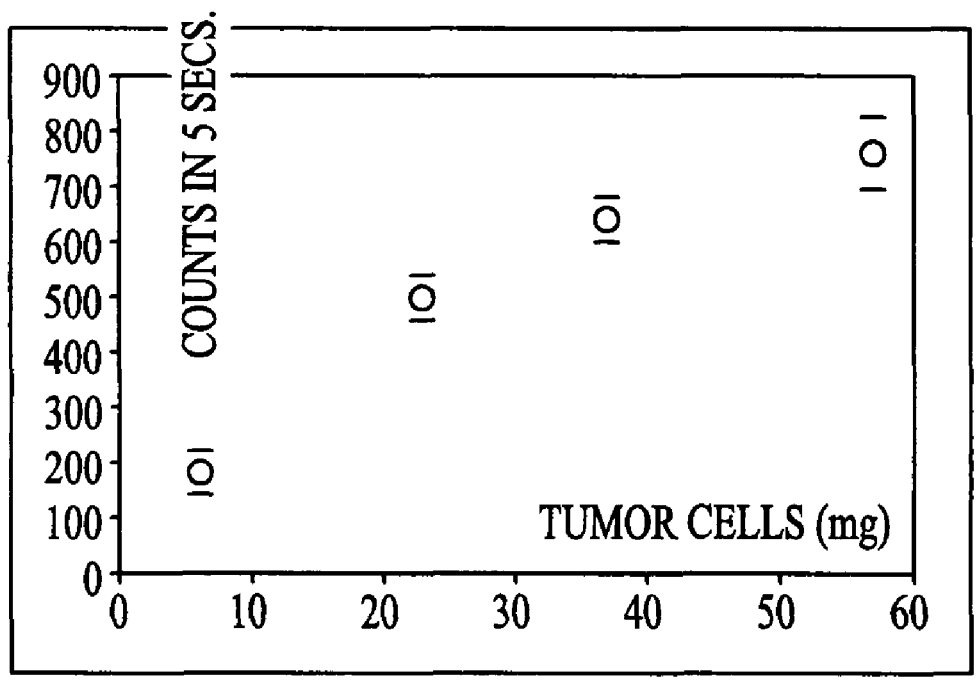
FIG. 12 is a graph which correlates the counts measured versus the number of labeled cells using the test apparatus of FIG. 11.

A prostate cancer cell line (LNCaP, CRL-1740, ATCC, Manassas, Va.) was used to establish the limits of detectability in terms of milligram of tumor. The radioisotope used, I-131, emits both gamma and beta rays similar to F-18. Cells were incubated with I-131 labeled J591 (antibody to prostate specific membrane antigen) for 2 hrs, then washed and the radioactivity was determined. In order to simulate tumors, as shown in FIG. 11, five small containers comprising 2 mm cylindrical recesses 62 were formed in a Lucite slab 64, (2 with diameters of 2 mm and 3 with diameters of 4 mm). These recesses 62 were then filled with labeled cells (simulated tumor) 66 and were covered by a thin plastic tape to allow beta rays to penetrate. Radioactivity counts were determined using a well counter, and the mass of each simulated tumor 66 was determined. A beta probe 16 incorporating the detection assembly 20 as described herein was placed on top of each simulated tumor 66 in the manner as shown in FIG. 11. Counts were collected for 5 sec and recorded in triplicate. This experiment was repeated 3 times with background sources of 0.63, 1, and 2.2 mCi of I-131 placed beneath the tumors. FIG. 12 is a graph showing data collected, demonstrating that a 5 mg tumor was detectable in presence of significant background radiation.

There were 20 nCi per one million cells. The 2 mm diameter containers contained 6 mg of tumor cells, and the 4 mm diameter containers contained 23, 37 and 57 mg of tumor cells, respectively. The beta probe counts in 5 sec were 180±40, 498±43, 641±38, and 762±65, respectively. These counts were not affected by the background gamma rays. The background gamma rays generated 39 counts in 5 sec when 2.2 mCi of source was present 5 mm below the beta probe.

These studies demonstrated that superficial tumors as small as 6 mg are detectable even in presence of gamma rays from a nearby 2 mCi source of I-131, thus demonstrating that the beta probe described herein is ideal for detection of small tumor residues utilizing FDG.

Example 2

Monoclonal antibody MX35 reacted with epithelial ovarian cancer was labeled with I-131. The labeling efficiency of the radioantibody was determined to be 92.6%. Six week old mice (n=3) (balb c/nu/nu) were injected intraperitoneally and subcutaneously with the human ovarian cancer cell line PR-428 (CRL-11732, ATCC). This cell line immuno-histologically expressed the MX35 antigen. The tumors weighed from about 0.5 to 2.0 grams. 25 mCi per 25 mg of labeled antibody were injected intravenously into the tail vein of each mouse. Probe counting was conducted 2, 5, and 7 days after Mab injection. Pentobarbital anesthesia was used and the tip of the probe 16 was placed on the surface of the skin at different locations on the body for the duration of 2 seconds per count.

I-131 labeled MX35 monoclonal antibody showed high accumulation in the tumors after 2 days post injection. The average beta probe count was 115 cps on top of the tumor, and from 10 to 30 cps 5 mm away from the tumors. This test showed that a tumor can be detected with the beta probe 16 even when there is intervening soft tissue covering the tumor.

Example 3

Figure 13:
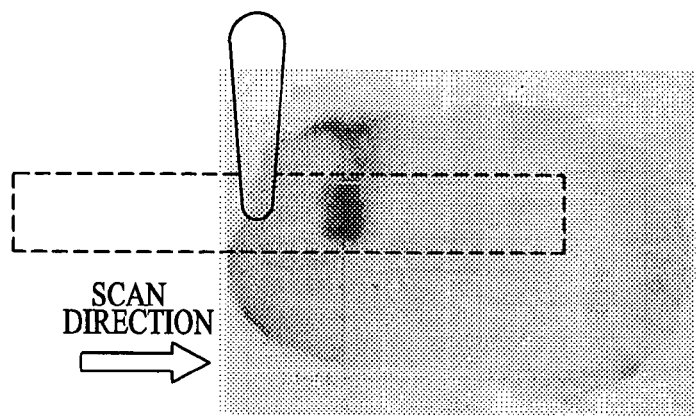
FIG. 13 shows a section of a rat's brain histologically stained with thionin along with the scan direction of a beta probe incorporating features of the invention.
Figure 14:
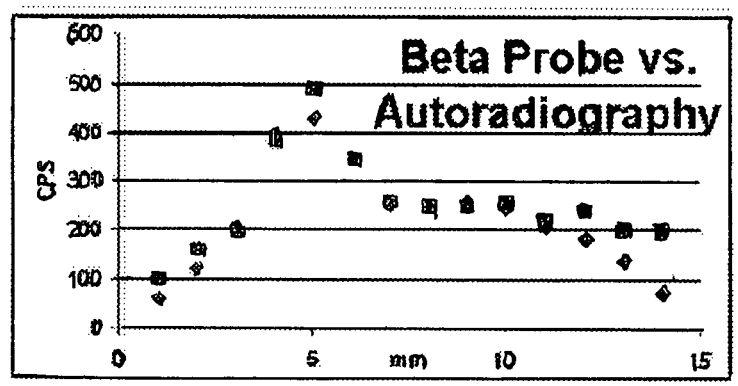
FIG. 14 is a graph showing the count profiles from the probe incorporating features of the invention obtained by scanning the upper one fourth of the coronal surface of a rat with a labeled tumor.

C6 (CCL-107, ATCC) rat glioma cells ($5$–$10 \times 10^5$) were implanted into the right hemisphere of Wistar rats. After 10-14 days of tumor growth, animals were fixed in a stereotactic frame, and FDG was then delivered as an intravenous bolus (5-20 mCi/kg). Sixty minutes latter the beta probe 16 was positioned perpendicular to the surface of both normal tissue and tumor implanted hemisphere. The counts over the tumor were consistently higher (120-140 counts/min/mCi injected, n=3 rats). The rats were sacrificed and the brains were removed and cut coronally at the center of the tumor along the same line that the probe 16 measurements were obtained. The upper ¼ of the coronal cut surface was then scanned and radioactive counts were recorded for one minute by the probe 16. Frozen sections of the brain (20 um) were then cut and thaw mounted on a gelatin-coated cover glass. Autoradiograms were generated, digitized and the optical densities were recorded by scanning the autoradiogram (1 mm sections). FIG. 13 shows a section of the rat's brain, adjacent to the one autoradiograph, histologically stained with thionin. The pattern of the tumor shown and that in the autoradiogram are closely correlated. The area scanned by the probe is shown in the upper ¼ of the image. Autoradiogram of the rat's brain section tumor with high accumulation of F-18 labeled FDG is shown in the upper part of the picture. This autoradiogram was digitized and the profile of the optical density over the area scanned by the probe was calculated. The average size of the tumor was 2 mm in diameter and 5 mm in depth and was correlated with histologic site of the tumor. The count profiles from the probe, obtained by scanning the upper one fourth of the coronal surface, correlated with the profile of the optical density of digitized autoradiogram is shown in FIG. 14. The profile of the radioactive counts obtained by horizontal scanning of the probe is shown by the diamonds. The profile of the optical density of the autoradiogram in the region scanned by the probe is shown by the squares. Both profiles showed the localization of the center of the tumor at 3 mm to the right to the midline of the brain and estimated the tumor width to be 3 mm. This test demonstrates that a small tumor ~1 mm labeled with FDG can be located by the beta probe.

Example 4

Figure 15:
FIG. 15 is a PET scan of a patient with melanoma on the neck.
Figure 16:
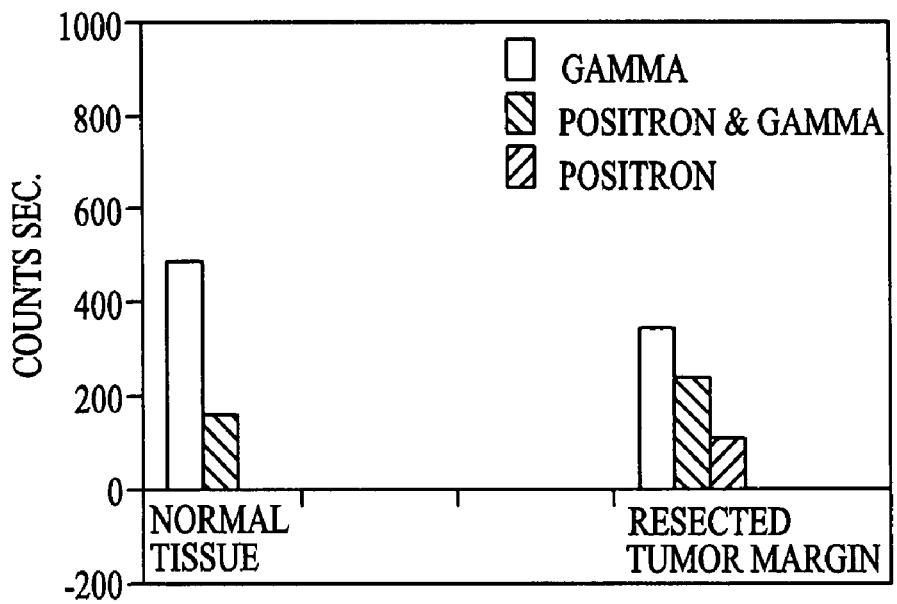
FIG. 16 is a graph showing radiation counts of a beta and a gamma detector on the residue of cancerous tissue after removal of the neck melanoma shown in FIG. 15.

FIG. 15 is a PET scan of a patient with melanoma on the neck. The bulk of the tumor was then removed from the patient and the resected margins were scanned using the beta probe 16. The beta probe 16 found occult cancerous tissue at the margins. Radiation counts were measured by both the gamma and the beta probe. The normal tissue had no positron activity, but there was activity at the margins of resection after removal of the tumor. In one area on the base of skull the beta probe registered high activity compared with the normal tissue (FIG. 16). Final pathology demonstrated microscopic-positive margins that would have otherwise not been identified by the surgeon. Only the use of the beta probe prevented this cancer tissue from being left behind. The active margins most probably would have evolved into a reoccurrence of cancer.

In use the probe will be exposed to body temperatures from about 25 to about 37° C. Therefore calibration curves were obtained at 37, 35, 33, 30, 27 and 25° C. to generate sensitivity and dark current plots. Four alternative methods were employed to achieve reliable count rates that are independent of the temperature of the field of operation. These methods are as follows:

Method #1: A small thermocouple 26 is mounted to the back of the module in contact with the SSPM 12 in order to measure the temperature in real time. A sensitivity plot vs temperature is then used to generate a look-up table for use in the probe operational software in the data processing unit 32 to correct for the effect of the temperature in real time.

Method #2: Real-time measurement of temperature can be made while varying the voltage in order to achieve constant sensitivity in the 25 to 37° C. range. The detector with temperature sensor 26 is inserted in a radioactive source at different temperatures and the working voltage is adjusted to achieve a constant output. Inclusion of this table into the software allows the working voltage to be controlled in real time.

Method #3: Real Time Variation of the Pre-amplifier's Gain can be made while the voltage is kept constant and the gain of the pre-amplifier is varied to achieve a constant count rate across a range of temperatures between 25° and 37° C.

Method #4: an electronic cooler, such as a Peltier chip 28, is placed in thermal contact with the SSPM 12 in order to lower the temperature of the SSPM 12 (see FIGS. 2 and 3). A temperature sensing device 26, such as a thermocouple is employed to measure the SSPM's temperature, and an electronic feedback circuit 30 is used to maintain a constant temperature at, for example 15° C.

These techniques are believed to be suitable to result in a percent change of less than 10%. As an alternative approach, the detector module can include means to maintain the module at a fixed temperature. For example, the detector module can be enclosed in a jacket and held at the constant temperature of 37° C. or a miniature Peltier chip 28 can be placed on the back of the SSPM to control the temperature of the module by using a feedback circuit 30 that reads the temperature and turns the cooler on and off to maintain a predetermined constant temperature.

A further embodiment comprises an array of 4 by 4 silicon photomultiplier devices (16 devices). A readout circuit encodes position information from SSPM 12 devices into a 4-wire output. The four signals are then added together to provide energy information. The SSPMs 12 were coupled to a sheet of plastic scintillator 14 using an optical grease and irradiated with a Na-22 source. Output current pulses averaged about 0.1 ma. This relatively large output current pulse can be encoded using a charge division scheme consisting of resistor chains in the X and Y direction to encode position. The 16 SSPMs 12 are connected to the resistor junctions. The proportions of the currents flowing to the corners of the array are then converted to a voltage using 4 transimpedance amplifiers. It is possible that the high capacitance of each device (35 pf) may slow the scintillation pulse to the point of degrading the signal when the 16 devices are read-out in this fashion. Also, the large resulting input capacitance at the input of each of the four transimpedance amplifiers may need to be compensated to eliminate amplifier instability resulting in oscillation. However, both of these conditions are eliminated by using a separate, high-speed transimpedance amplifier for each of the 16 devices, converting the outputs to currents, and then feeding these currents into the resistor network encoder scheme referred to above. Another factor taken into consideration is gain matching between the devices. Because this is not provided by the manufacturer of the SSPM, a variable and independent bias voltage can be applied to each device and then the gain of the whole array normalized. A further embodiment comprises a readout board for 10×10 SSPMs in place of the 4×4 SSPM. The intrinsic uniformity of the beta cameras described herein is measured by scanning a flat uniform source of F-18 solution contained in a shallow dish. The result generated is reported as the ratio of the difference of the maximum counts/pixel and the minimum counts/pixel, over the average counts per pixel.

The tests were repeated in presence of various amounts of background radioactivity. First a glass bottle was filled with 2 liters of F-18 solution (total activity of 100 microCi) and placed under the beta camera; the image was acquired in 15 minutes. The energy window was set above the electronic noise. After this image was acquired, the average counts per pixel were measured. The energy threshold was then raised to one third of the highest energy channel, and the test was repeated. The sensitivity flat source was then placed under the beta camera, the background source was removed, and the sensitivity at the new energy threshold was measured. This procedure was repeated five times with the energy threshold raised each time until the highest channel was reached.

In order to determine the spatial resolution of the beta camera, expressed in terms of the smallest hole pattern visible on the image, a phantom was prepared comprising multiple 2 mm deep holes, with different diameters, drilled in a flat Lucite block. The diameters of the holes were 1, 2, 3 or 4 mm, with their center-to-center distance equal to twice their diameters. They were filled with I-131 in solution, and covered by thin plastic tape. A beta camera was placed on top of this phantom and images were acquired for different time durations (10, 30, 60, 300 seconds). A uniformity correction was then applied. This test was repeated at different specific activities (0.2, 0.5, 1, 2, uCi/ml). The same phantom was used to determine the fractional degree of deviation from straight line in the image pattern.

In addition, a set of phantom were used to determine the limit of tumor detection with the beta camera. A phantom of the normal tissue was made with a low radioactive concentration using a mixture of flour and solution of F-18 FDG. The more radioactive lesions were made in the same fashion. A large rectangular plastic container (60×30×20 cm) was filled with F-18 FDG and flour, and mixed to form a large piece of dough in the form of the human torso. One (1) gram samples of different areas of this phantom were used to measure its radioactive concentration in a well counter. The goal was to achieve a concentration of 0.2 microCi/cc. Various spheres of tumor phantoms (with radioactive concentration of 1 microCi/g) were then placed on or near the surface of the normal tissue phantom, the beta camera was placed over the simulated tumor for 30 seconds and an image acquired. The diameters of the simulated tumors were set at 3, 5, 7, 10, 15 mm. and the radiation levels in the tumors were set at 0.4, 0.6, 0.8, 1.5, and 2 microCi/g. To study the effects of thin layers of normal tissue that may be covering a superficial tumor, these experiments were repeated with layers of different thickness plastic (0.5, 1, 1.5, 2, 3, 5 mm) placed between the camera and the Lucite phantom and the simulated surgical procedures with a phantom were repeated.

Figure 17:
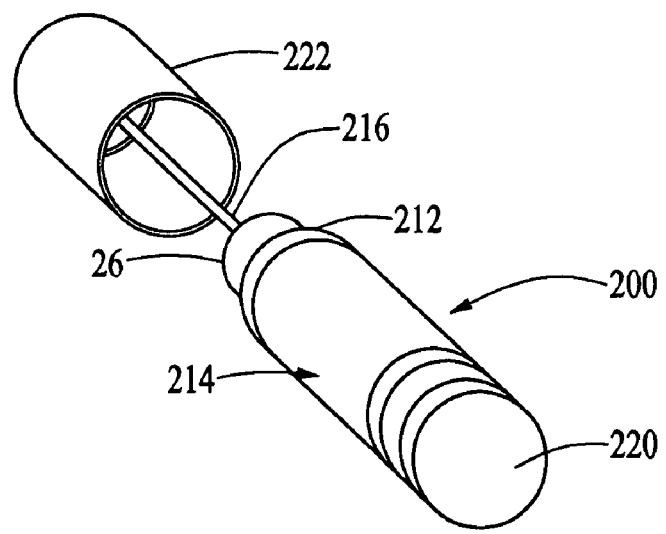
FIG. 17 is an expanded schematic view of a detector assembly incorporating features of the invention, for use in building very small beta probes, for example on the order of one millimeter diameter, or one-dimensional cameras.
Figure 18:
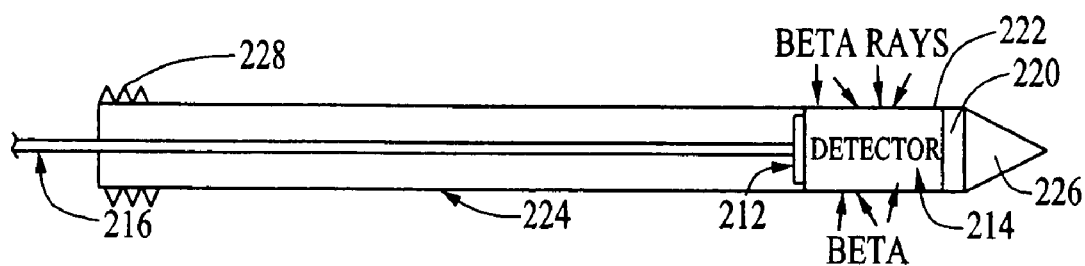
FIG. 18 is a side view of a biopsy probe incorporating the detector assembly of FIG. 17.
Figure 19:
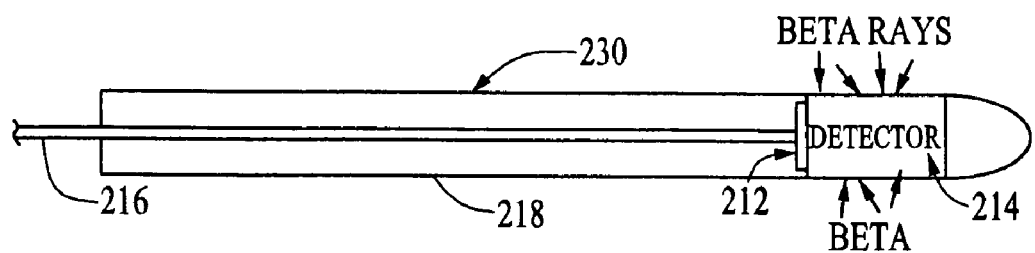
FIG. 19 is a side view of a catheter incorporating the detector assembly of FIG. 17.

Referring to FIG. 17, to prepare a probe 200 as described herein for use in a biopsy or intra-vascular radiation detection procedures a 1 mm diameter SSPM 212 (Photonique SA, Geneva,) was attached to a 5 mm long red plastic scintillator 214 (1 mm diameter, BC-430 Saint Gobain). The spectrum of the scintillation of light emitted by this red plastic scintillator 214 matches well with the spectral response of the SSPM 212 attached thereto. The emission spectrum of the scintillator peaks fairly sharply at 580 nm, where the detection efficiency of the SSPM is about 20%. A thin and flexible coaxial cable 216 (such as W. L Gore Ribbonized Coaxial or equivalent) was connected to the two leads of the SSPM 212. This cable 216 can be passed through a conventional cardiac catheter 218, such as shown in FIG. 19 approximately 160 mm long which is glued to the end of the SSPM using a bio-safe glue. An end-cap 220 of stainless steel, preferably 304 stainless, was attached to the scintillator end of the module and wrapped in 5 micron-thin stainless steel foil 222 (GoodFellow Corp.) (shown in FIG. 17 retracted so that the inner construction can be displayed). A preferred adhesive for attaching the foil to the stainless cap is a bio-safe epoxy such as Master Bond EP21LV or equivalent. In a preferred embodiment the diameter of the detector module is approximately 1.25 mm, and the length of the scintillator is about 5 mm. A biopsy probe 224 constructed as shown in FIG. 18 is inserted with or without the catheter 218 through biopsy needle (not shown), such as the BioPince Core Biopsy Needle, which has a 1.25 mm inner diameter, the biopsy probe 224 being designed to fit within the needle. The length of the needle (cannula) is about 5 mm longer than the standard 120 mm needle, so that a sharp distal end 226 on the detector 224 sticks out of the cannula during the exploration phase. While the construction such as shown in FIG. 2 is described, the dual probe such as in FIG. 3 can be used and any of the designs of FIGS. 7-10 can be incorporated in the probe. The biopsy probe 224 is placed inside a cannula and they are fixed together by a Luer-Lok® 228 (or any other suitable locking structure) on the proximal end of the probe 224, to form a Coaxial Introducer Needle/Probe assembly. The tip of the probe/cannula assembly has a sharp stainless steel tip 226 to cut through tissue so that the whole probe can approach and pierce through the lesion. The advancement of the biopsy probe 224 is stopped when the detector registers the maximum count rate of the beta rays within the lesion, or the camera shows a focal point of radioactivity along its axis. A safety lock (not shown) can then be advanced over the outer surface of the cannula so it contacts the skin, the Luer-Lok® 228 is twisted open and the probe 224 is retracted from the lesion, leaving the cannula tip in the lesion. A biopsy stylet can then be inserted through the conduit and the sample of the labeled tissue removed. The removed tissue sample can be counted again, ex-vivo, utilizing the beta probe 224 to ensure that it contains higher radioactive concentration before the procedure is terminated. The cannula can also be used as a conduit for delivery of a treatment media directly to the lesion or in close proximity of the diseased tissue. In another embodiment a dual detector module (FIG. 3) is used, therefore increasing the sensitivity compare to the use of single-detector module. In yet another embodiment a one-dimensional array of single or dual detector modules are used for obtaining the distribution of the beta radiation profile.

FDG-PET Characterization of Plaque Inflammation

Several groups have demonstrated that FDG accumulates in inflamed atherosclerotic specimens in rabbit models of atherosclerosis. In a study performed with Watanabe heritable hyperlipidemic (WHHL) rabbits, Ogawa, et al. showed that 18F-FDG uptake correlate with the number of macrophages within the atherosclerotic lesions (R=0.81, P<0001).

Applicant has found that non-invasive FDG-PET measurements correlate strongly with inflammation in experimental atherosclerotic lesions. In that study, inflamed atherosclerotic lesions were induced in nine male New Zealand white rabbits via balloon injury of the aorta-iliac arterial segment and exposure to a high cholesterol diet. Ten rabbits fed standard chow served as controls. Three to six months following balloon injury, the rabbits were injected with FDG (1 mCi/kg) and 3 hours thereafter the aortic uptake of FDG was assessed. Biodistribution of FDG activity within aortic segments was obtained using standard well gamma counting. FDG uptake was also determined non-invasively in a subset of six live atherosclerotic rabbits and five normal rabbits, using PET imaging and measurement of standardized uptake values (SUV) over the abdominal aorta. Plaque macrophage and smooth muscle cell density were determined by planimetric analysis of RAM-11 and smooth muscle actin staining, respectively.

Co-registered PET&CT images demonstrated increased uptake of FDG in atherosclerotic aortas compared to control aortas. Further, well counter measurements of FDG uptake was significantly higher within atherosclerotic aortas compared to control aortas (P<0.001). In parallel with these findings, FDG uptake, as determined by PET, was higher in atherosclerotic aortas (0.68±0.06 vs. 0.13±0.01, SUV atherosclerotic vs. control, P<0.001). Moreover, macrophage density, assessed histologically, correlated with well-counter measurements FDG accumulation (r=0.79, P<0.001) as well as the non-invasive in vivo (PET) measurements of FDG uptake, (r=0.93, P<0.0001). Importantly, FDG uptake did not correlate with either smooth muscle cell staining, vessel wall thickness, or plaque thickness of the specimens. These data show that FDG accumulates in macrophage-rich atherosclerotic plaques and demonstrate that vascular macrophage activity can quantified non-invasively with FDG-PET. As such, measurement of vascular FDG uptake with PET holds promise for the non-invasive characterization of vascular inflammation.

An intravascular beta ray detection probe 230 offers several advantages over conventional PET imaging. The resolution of the probe is significantly better than PET (2 vs. 6 mm). Also, in contrast to PET, the intravascular detection of short-range positrons is not affected by myocardial uptake of FDG. This is attributed to the fact that the beta probe detects beta particles (which travel less than 2 mm), and therefore, myocardium-derived particles do not reach the probe. On the other hand, PET detects annihilation photons, which traverse many centimeters through tissue. An intravascular detector enables precise localization of VP during the same sitting as diagnostic coronary angiography. This enables the local delivery of plaque-stabilizing therapy in a way that non-invasive techniques do not.

In order to prove this concept with a beta probe, a PMT-optical fiber designs, was built by the applicant and the PMT-optical fiber based beta-ray detector probe was used to examine the feasibility of intravascular detection. This earlier design of a flexible beta probe had a diameter of 1.6 mm and length of 40 cm. This probe was selectively more sensitive to positrons than gamma rays or annihilation photons. To construct this probe, a 1 mm diameter, 2 mm long plastic scintillator was optically connected to a PMT via a 1 mm diameter, 40 cm long optical fiber, and was covered by aluminized Mylar (thickness=100 microns) acting as a reflector of the scintillation light. A commercially available computerized data acquisition system (Node Seeker-720™, IntraMedical, Inc.) was used to collect and display the counts. The efficiency of that probe, measured by placing a point source of F-18 in touch with its sensitive tip, was only about 0.2%. FIG. 19 shows a vascular probe 230 similar in design to the biopsy probe of FIG. 18. The intravascular probe 230 has an SSPM 212 which receives a light pulse from a plastic scintillator 214. The electrical output of the scintillator 214 is fed, by a cable 216 threaded through a catheter 218, to a digital signal processor 22 and then to a display 42. Preliminary testing of the novel detector incorporating features of the invention incorporating SSPMs 212 demonstrated significant improvement in efficiency (up to about 15% efficiency) for a catheter 218 of 160 cm length. This device also had the added safety of low-voltage bias.

To prove the concept of using the intravascular probe 230 to detect labeled plaque an animal model was used. Atherosclerotic lesions were induced in New Zealand rabbits with a balloon injury to the infradiaphragmatic aorta followed by a high cholesterol diet. At 10 weeks, 37 MBq/kg FDG was administered to 4 rabbits with atherosclerotic lesions as well as to 3 control rabbits. 3-4 hours after FDG, the rabbits were sacrificed, and aortas removed as a single segment. The flexible intravascular beta probe 230 described above was inserted into the aorta. Measurements were made in triplicate, (at 2 s/measurement), at sites of grossly visible plaque and at non-injured sites in the cholesterol fed rabbits, as well as in corresponding areas in the control aorta. The queried aortic segments were then excised and examined using standard well counting. Activity determined by the catheter correlated with well counting measurements, (r=0.89, P<0.001). Moreover, atherosclerotic plaques were readily distinguished from non-injured regions by the beta probe, (11.9±2.1 [n=9, range 9.7-15.3] vs. 4.8±1.9 [n=14, range 1.3-7.3], cps in atherosclerotic vs control regions, P<0.001).

This animal study demonstrated that while applicant's prior art PMT-optical fiber based intra-vascular beta probe, together with FDG, had promise for the in vivo detection of vulnerable plaques, to be practical for effective use in humans it required higher sensitivity, better flexibility, and a greater efficiency. This has now been met by the intravascular probe 230 described herein above.

In a related area, Shen et al. showed that optical detection of breast cancer in the milk duct can be performed using a fiberoptic ductoscopy (Shen, K-W, Wu J, Lu J-S, et al. "Fiberoptic Ductoscopy for Patients with Nipple Discharge", Cancer, 89, pp 1512-1519 (2000). In addition to intra-vascular applications for finding atherosclerotic plaques described above, the intravascular probe 230 or other one dimensional beta cameras built with SSPMs as described above can be used for intra-ductal detection of cancer in the breast, after injecting the patient with F-18 FDG, or any other beta emitting radio-tracers used for cancer detection. In addition, this probe can be used in intra-vascular detection of cancer by insertion into tumor vasculature, its movement guided by x-ray or ultrasound. Other body cavities can be used as access ports for this flexible radiation detection probe for detection of abnormal tissue in other organs; For example, the bladder can be accessed through urethra; the brain can be accessed through the nasal cavity, etc.

The beta probe or one-dimensional beta camera described above for use in biopsy examination or as an intravascular catheter, for passage through blood vessels to locate labeled plaque or vascular inflammation can also be passed through a 5 mm-12 mm port in a laparoscope to detect, or map a tumor being resected by laparoscopic surgery.

Figure 23:
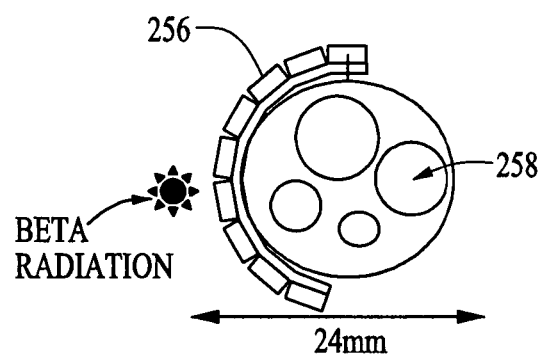
FIG. 23 shows an array of SSPMs on the exterior surface of a scope, such as an endoscope, for insertion in a body orifice.

Esophageal cancer is very deadly—the American Cancer Society estimates that in 2006 there will be 14,550 new cases and 13,770 deaths in the United States alone. Patients are often diagnosed only after they present with symptoms, at which point the cancer is usually well advanced. If the disease is caught in the early stages, however, the prognosis can be quite good. Early detection is most likely to occur in populations being screened for the development of esophageal neoplasms. Patients diagnosed with Barrett's esophagus, the precursor lesion for esophageal adenocarcinoma, typically undergo regular surveillance for the progression of their condition to cancer. Unfortunately, current diagnostic methods which generally comprise anatomically guided biopsy for histological analysis are not accurate at detecting early stage disease. Histopathology is the only way to distinguish between the first stages of progression and malignancy, and thus biopsies are taken essentially at random. Applicant has conducted preliminary studies on patients injected with FDG and biopsied for measurement of the FDG uptake in tumor, Barrett's cells and normal tissue. This study shows that FDG uptake is an indicator of grade of the disease. In light of this discovery, a further alternative of the beta cameras described herein, is to prepare the array of the scintillators 14 as separate SSPM/scintillator units 250 and mounting them on the surface of a flexible membrane 252 to form a flexible detector arrangement 256 such as shown in FIG. 5. This membrane 252 can then be wrapped around the external surface of a scope 258, such as endoscope, for example in the manner shown in FIG. 23, so that diseased tissue in the esophagus can be located, removed and biopsied. The cancerous tissue can then be removed or various topical therapies can be applied directly to labeled tissue in the esophagus.

As a still further alternative, the imaging of metabolic function, as indicated by increased radiotracer uptake, is believed to be a more accurate method of detection early cancer and dysplasia, and therefore indicate appropriate regions to biopsy. Localized detection of $^{18}$FDG was conducted using an endoscopic-based beta camera, which was brought into direct contact with the tissue being surveyed. Using a single-channel probe (a single SSPM/scintillator modulator 250) the area that can be surveyed is limited by the size of the probe tip. Exploring the esophagus with such a probe is therefore time-consuming. However, because a beta camera combines counts from an array of detectors and produces a scan of a larger field of view the entire esophagus can be scanned relatively quickly. Further, a non-planar or curved imager is superior to a planar camera, because it will conform better to the curved wall of the esophagus or other body passage.

The embodiment is not limited to use in the esophagus and can be inserted in other body orifices. For example, a beta camera array can also be introduced rectally to map a labeled prostate, aid in imaging the prostate and conducting a biopsy of the rectal wall as well as for post prostatectomy examination in patients with elevated PSA.

We have developed endoscopic positron emission detectors for endoscopic imaging with PET radiotracers. The development of highly sensitive endoscopic based positron emission imaging coupled with clinically available PET radiotracers (e.g. 18 fluoro-2-deoxyglucose (FDG)) offers the potential for endoscopic molecular imaging. There are detectable differences in FDG uptake between normal, dysplastic and cancerous esophageal tissue and these differences are detectable using endoscopic based positron emission molecular imaging.

To demonstrate the utility of the above described endoscopic procedure, immediately following FDG administration and performance of a PET scan, patients with esophageal malignancies were evaluated endoscopically along with the performance of multiple biopsies taken from normal and abnormal appearing esophageal tissue. FDG expression in the biopsy samples was measured using a well-counter (the standard measuring device for FDG expression in tissue samples) and a miniature flexible positron emission detector such as incorporated in the endoscopic positron-sensitive imaging system described herein. The decay corrected counts per minute per mg of tissue were calculated based on the Picounter reading, time from the initial FDG injection and the weight of the biopsy specimen. Endoscopic biopsies were classified blindly by an experienced esophageal histopathologist (WMW), as normal squamous esophageal mucosa, intestinal metaplasia, dysplasia or invasive cancer. All results were normalized using the normal esophageal squamous epithelium counts per minute per mg as the reference point and expressed as mean+/−standard error of mean. Decay corrected counts per minute were correlated with histology. For the purposes of analysis, intestinal metaplasia and dysplasia were grouped together as premalignant lesions. Endoscopic biopsy FDG level as measured using the well-count was correlated with the measurements of the same tissue using the miniaturized positron emission detector.

Seven patients were studied with between 8-14 esophageal biopsies sampled per patient. Three patients (1 cancer, 2 dysplasias) with negative PET scans had evidence of elevated FDG expression in their abnormal biopsies as compared to normal tissue. Six of seven patients showed a significant difference between endoscopic biopsy FDG levels for normal, intestinal metaplasia (IM)-dysplasia and invasive cancer. There was a strong correlation between FDG levels in biopsies as measured by standard well-count and the miniaturized flexible positron emission detector (r=0.85). Based on the data collected it was demonstrated that there is a differential expression in FDG levels between normal, dysplastic and invasive esophageal cancer. In three patients in whom the PET scan was read as negative the direct measurement of positron emission was correctly able to identify cancer and dysplasia. This confirms the superiority of our endoscopic radio-detection approach to conventional PET scan. There is a strong correlation between biopsy FDG expression as measured by standard technique and the above described miniaturized flexible positron emission detector, supporting the utility of endoscopic positron emission molecular imaging for esophageal dysplasia and the endoscopic evaluation with a radiation detection probe, in conjunction with radionuclide markers for enhancing selective endoscopic biopsy.

Beta camera arrays as described herein are not limited to use in vivo. They can also be formed, by a tiling technique or, applied to a flexible backing, formed into a trough or cup shape for use in examination of the margins of resected tumors or prostate tissue placed therein to determine, by the detection of beta-ray emitting labeled cells, if the tumor cells appear to be on or near the margin of the extracted tissue.

Still further, the techniques and devices described herein are not limited to beta or gamma detection. One skilled in the art will recognize that other radioactive emissions, for example, alpha rays, can be detected using similar arrangement with alpha-sensitive photo emitters.

In summary, applicant has disclosed various embodiments of radiation detection probes and radiation detection cameras which are capable of detecting minute quantities of radioactive-labeled sites within the body so these tissues can be located, removed, and verified in vitro, based on beta or gamma emissions from those labeled tissue. The system can include corrections or adjustments for temperature so that the readings are normalized. While examples are given for use in locating cancer cells, inflamed or modified tissue or vulnerable plaque the utility of the invention is not limited thereto and can be used to locate and map any site, any specific tissue or any abnormal tissue, within the body that can be selectively labeled with radiation emitting materials.

We claim:

1. A beta camera for detecting the presence of radiation emitted from labeled sites in the human body comprising:
   a plastic scintillator film sensitive to beta radiation having a front surface for receiving emissions from radioactive labeled sites,
   an array of multiple silicon photomultipliers, each of said solid state or silicon photomultipliers having a front surface in direct optical communication with a rear surface of the plastic scintillator,
   electronic signal output means on a rear surface of each of said silicon photomultipliers, and
   an electronic circuit located to receive the electronic signal output from each of said silicon photomultipliers,
   the combination of at least the plastic scintillator and array of silicon photomultipliers being encased in a capsule, a portion of the capsule covering the front surface of the plastic scintillator having a thickness which allows transmission of the beta radiation to the front surface of the plastic scintillator, portions of the capsule on the rear and side surfaces acting as a barrier to light and beta radiation.

2. The beta camera of claim 1 further including data processing means to convert output signals from the electronic circuit to a visual image for display on a video monitor, the display indicating the level of radiation being emitting from labeled sites immediately adjacent to the front surface of the plastic scintillator.

3. The beta camera of claim 1 further including data processing means to convert output signals from the electronic circuit to a visual image for display on a video monitor, the display indicating the location within a surgical site being scanned of the labeled tumor cells emitting radiation, the level of radiation being emitted from the labeled sites immediately adjacent to the front surface of the plastic scintillator and a map of the levels of radiation measured from different locations in the surgical site.

4. The beta camera of claim 1 wherein the plastic scintillator has multiple tapered extensions on a rear surface thereof, the number of tapered extensions being the same as the number of silicon photomultipliers, each one of the multiple extensions being connected to a silicon photomultiplier adjacent thereto by the optical glue.

5. The beta camera of claim 1 wherein optical communication between the silicon photomultipliers front surfaces with a rear surface of the plastic scintillator is provided by a light transmitting film.

6. The beta camera of claim 5 wherein the light transmitting film has multiple tapered extensions on a rear surface thereof, the number of tapered extensions being the same as the number of silicon photomultipliers each one of the multiple extensions being connected to a silicon photomultiplier adjacent thereto to transmit optical signals thereto.

7. The beta camera of claim 1 wherein the radiation labeled sites within the human body are tumor cells, inflamed or abnormal tissue or atheromous plaque.

8. The beta camera of claim 1 wherein the beta camera is mounted on or for placement through a biopsy needle, is located in the distal end of a vascular catheter, is configured for placement through the port in a laparoscope or into an open surgical site against exposed tissue.

9. The beta camera of claim 1 further including vacuum means attached to or on the surface thereof for applying a suction force to adjacent tissue surfaces to provide intimate contact of the outer surface to the adjacent tissue to aid in image acquisition.

10. The beta camera of claim 1 further including a digital visible-light camera for obtaining optical images of adjacent tissue.

11. The beta camera of claim 1 further including marking means for application of observable indicia onto the surface of adjacent tissue.

12. A beta camera for detecting the presence of radiation emitted from labeled sites in the human body comprising:
   a plastic scintillator film sensitive to beta radiation having a front surface for receiving emissions from radioactive labeled sites,
   an array of multiple silicon photomultipliers, each of said silicon photomultipliers having a front surface in direct optical communication with a rear surface of the plastic scintillator,
   electronic signal output means on a rear surface of each of said silicon photomultipliers, and
   an electronic circuit located to receive the electronic signal output from each of said silicon photomultipliers,
   components of the beta camera arranged so that beta rays are transmitted through the front surface of the plastic scintillator in preference to transmission of the beta radiation to the rear and side surfaces of the array of multiple silicon photomultipliers and the plastic scintillator.

* * * * *